United States Patent
Smith

(10) Patent No.: US 7,335,771 B2
(45) Date of Patent: Feb. 26, 2008

(54) QUINACRIDONE DERIVATIVES AS LABELLING REAGENTS FOR FLUORESCENCE DETECTION OF BIOLOGICAL MATERIALS

(75) Inventor: John Anthony Smith, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 433 days.

(21) Appl. No.: 10/479,659

(22) PCT Filed: May 30, 2002

(86) PCT No.: PCT/GB02/02537

§ 371 (c)(1),
(2), (4) Date: Dec. 1, 2003

(87) PCT Pub. No.: WO02/099432

PCT Pub. Date: Dec. 12, 2002

(65) Prior Publication Data

US 2004/0171014 A1    Sep. 2, 2004

(30) Foreign Application Priority Data

Jun. 4, 2001   (GB) ................... 0113434.5

(51) Int. Cl.
C07D 221/18   (2006.01)
A61B 5/06   (2006.01)
A61B 5/1468   (2006.01)

(52) U.S. Cl. .................. 546/58; 424/9.34; 424/9.6; 514/280

(58) Field of Classification Search ............... 546/58; 424/9.34, 9.6; 514/280
See application file for complete search history.

(56) References Cited

U.S. PATENT DOCUMENTS 5,713,999 A  *  2/1998  Badejo et al. ............... 106/495
5,755,875 A  *  5/1998  Zambounis et al. ......... 106/498

OTHER PUBLICATIONS

Thomas Faller et al 1997, A novel acridone derivative for the fluorescence tagging and mass spectrometric sequencing of peptides.*
English abstract, Honig Marcia et al Dil and DiO: versatile fluorescent dyes for neuronal labelling and pathway tracing. 1989.*
W.K. Schlage et al Vital cell labelling for the detection of Invasive growth in the chick Embryo sjin Invasion assay, 1999.*

Klein, G., et al. "A fluorescent metal sensor based macrocyclic chelation" Chemical Communications, vol. 7, No. 6, Mar. 21, 2001 pp. 561-562.
Liu, P., et al. "Luminescence properties of novel soluble quiancridones" Journal of Photochemistry and Photobiology A: Chemistry vol. 137, Dec. 4, 2000 pp. 99-104.

* cited by examiner

*Primary Examiner*—Rita Desai
(74) *Attorney, Agent, or Firm*—Yonggang Ji

(57) ABSTRACT

Disclosed are new quinacridone dye derivatives having characteristic fluorescence lifetimes. Also disclosed are methods for labelling target biological materials employing the quinacridone dyes and use of the labelled materials in biological assays. The quinacridone derivatives have the following structure:

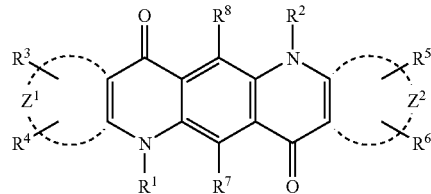

in which $Z^1$ and $Z^2$ independently represent the atoms necessary to complete one ring, two fused ring, or three fused ring aromatic or heteroaromatic systems, each ring having five or six atoms selected from carbon atoms and optionally no more than two atoms selected from oxygen, nitrogen and sulphur; $R^3$, $R^4$, $R^5$, $R^6$, $R^7$ and $R^8$ are independently selected from hydrogen, halogen, amide, hydroxyl, cyano, nitro, mono- or di-nitro-substituted benzyl, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2—)_n$Y; $R^1$ and $R^2$ are independently selected from hydrogen, mono- or di-nitro-substituted benzyl, $C_1$-$C_{20}$ alkyl, aralkyl, the group -E-F and the group —$(CH_2—)_n$Y; E is a spacer group, F is a target bonding group; Y is selected from sulphonate, sulphate, phosphonate, phosphate, quaternary ammonium and carboxyl; and n is an integer from 1 to 6.

The invention also relates to a set of different fluorescent quinacridone dye derivatives, each dye having a different fluorescence lifetime, the set of dyes being particularly useful for multiparameter analysis.

6 Claims, 4 Drawing Sheets

Absorbance and emission of 6-{7,14-dioxo-2,9-disulpho-7,14-dihydro-12H-quino[2,3-b]acridin-5-yl}hexanoic acid in PBS

Fluorescence lifetime decay plots

A: Diethyl ester of 6-{2,9-dimethoxy-12-(5-carboxypentyl)-7,14-dioxo-7,14-dihydro-12H-quino[2,3-b]acridin-5-yl}hexanoic acid B: 6-{2,9-dibromo-12-(5-carboxypentyl)-7,14-dioxo-7,14-dihydro-12H-quino[2,3-b]acridin-5-yl}hexanoic acid C: 6-{12-ethyl-7,14-dioxo-2,9-disulpho-7,14-dihydro-12H-quino[2,3-b]acridin-5-yl}hexanoic acid Fluorescence lifetime decay plot of 6-{7,14-dioxo-2,9-disulpho-7,14-dihydro-12H-quino[2,3-b]acridin-5-yl}hexanoic acid and its conjugate with ovalbumin

- 6-{7,14-dioxo-2,9-disulpho-7,14-dihydro-12H-quino[2,3-b]acridin-5-yl}hexanoic acid + 6-{7,14-dioxo-2,9-disulpho-7,14-dihydro-12H-quino[2,3-b]acridin-5-yl}hexanoic acid − Ovalbumin conjugate

QUINACRIDONE DERIVATIVES AS LABELLING REAGENTS FOR FLUORESCENCE DETECTION OF BIOLOGICAL MATERIALS

CROSS REFERENCE TO RELATED APPLICATIONS

This application is a filing under 35 U.S.C. § 371 and claims priority to international patent application number PCT/GB02/02537 filed May 30, 2002, published on Dec. 12, 2002 as WO02/099432, and to foreign application number 0113434.5 filed in Great Britain on Jun. 4, 2001, the entire disclosures of which are hereby incorporated by reference.

The present invention relates to new fluorescent labels. In particular the invention relates to new quinacridone derivatives that can be used as labels for attachment to target biological materials. The invention also relates to methods for labelling target biological materials and use of such labelled materials in biological assays.

There is an increasing interest in, and demand for, fluorescent labels for use in the labelling and detection of biological materials. Fluorescent labels are generally stable, sensitive and a wide range of methods are now available for labelling biomolecules. Typically, the emission spectrum of a fluorescent dye is a characteristic property of the is dye. Measurements of the fluorescence intensity, the fluorescence lifetime, or fluorescence polarisation may be used in the detection and quantitation of materials labelled with that dye. One problem with measurements of fluorescence intensity as a means of detecting and/or measuring the concentration of a fluorescent labelled biomolecule is that background fluorescence may interfere with the measurement. Thus, in order to obtain improvements in the sensitivity of fluorescence detection, it is highly desirable to improve the signal-to-noise ratio.

One means of overcoming the problem of background noise has been through the use of long wavelength dyes, for example, the cyanine dyes Cy™5 and Cy7, as disclosed in U.S. Pat. No. 5,268,486 (Waggoner et al). These dyes emit in the 600-750 nm region of the spectrum, where background fluorescence is much less of a problem. Another means of improving the signal-to-noise ratio in fluorescence measurements is through the use of time-resolved fluorescence, for example by using fluorescent labels based on lanthanide chelates, eg. $Eu^{3+}$ and $Tb^{3+}$ (Selvin et al, U.S. Pat. No. 562,282). In time-resolved fluorescent labels, the fluorescence emission is typically longer than that of the background fluorescence, which may therefore be gated out using appropriate instrumentation.

Linear trans-quinacridones are highly fluorescent and quinacridone derivatives have been developed as organic pigments (U.S. Pat. No. 2,844,484 (Reidinger, A. D. et al), U.S. Pat. No. 3,386,843 (Jaffe, E. E. et al)), for use in high sensitivity photosensors and organic light-emitting diodes and optical probes. Liu, P-H et al (J.Photochem.Photobiol., (2000), 137, 99-104) have synthesised a number of 5,12-N, N'-dialkyl-2,9-dialkoxy quinacridones and have investigated their spectral properties. Klein, G. et al (J.Chem.Soc.Chem-.Commun., (2001), 561-2) have prepared ethylenediamine functionalized quinacridone derivatives for use as fluorescent metal sensors.

Val'kova, G. et al (Dokl. Akad. Nauk. SSR, (1978), 240(4), 884-7) have measured the fluorescence lifetime of quinacridone, however, to date, there appear to be no reports relating to the use of quinacridones as dyes suitable for labelling and the detection of biological materials such as nucleic acids, peptides, proteins, antibodies, drugs, hormones, cells and the like. The present invention therefore describes modifications of the quinacridone chromophore, to produce a range of quinacridone derivatives which are useful for labelling biological materials. The quinacridone derivatives of the present invention moreover provide a valuable set of fluorescent labels having a common core structure and which are particularly useful for multiparameter analysis. In each dye of a set of dyes, the absorption and emission spectra remain essentially the same, whilst the fluorescence lifetimes of the dyes vary. Thus, it is possible to use a common excitation source and determine the fluorescence lifetimes at the same emission wavelength, thereby simplifying requirements for detection instrumentation used in multiparameter experiments. Another advantage of the dyes according to the present invention is that the fluorescence emission wavelengths and lifetimes of the quinacridone derivatives are generally longer than the lifetimes of other fluorescent labels as well as naturally occurring fluorescent materials, such as proteins and polynucleotides, thereby allowing easy discrimination from background fluorescence in assays utilising such dyes.

Accordingly in a first aspect, the present invention provides use of a reagent for labelling a target biological material, wherein said reagent is a dye of formula (I):

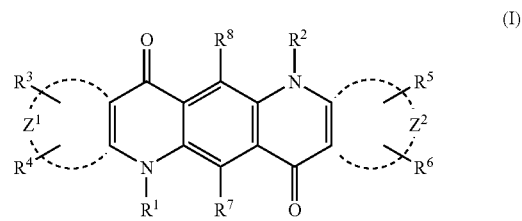

wherein:

groups $R^3$ and $R^4$ are attached to the $Z^1$ ring structure and groups $R^5$ and $R^6$ are attached to the $Z^2$ ring structure;

$Z^1$ and $Z^2$ independently represent the atoms necessary to complete one ring, two fused ring, or three fused ring aromatic or heteroaromatic systems, each ring having five or six atoms selected from carbon atoms and optionally no more than two atoms selected from oxygen, nitrogen and sulphur;

$R^3$, $R^4$, $R^5$, $R^6$, $R^7$ and $R^8$ are independently selected from hydrogen, halogen, amide, hydroxyl, cyano, nitro, mono- or di-nitro-substituted benzyl, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2—)_nY$;

$R^1$ and $R^2$ are independently selected from hydrogen, mono- or di-nitro-substituted benzyl, $C_1$-$C_{20}$ alkyl, aralkyl, the group -E-F and the group —$(CH_2—)_nY$;

E is a spacer group having a chain from 1-60 atoms selected from the group consisting of carbon, nitrogen, oxygen, sulphur and phosphorus atoms and F is a target bonding group;

Y is selected from sulphonate, sulphate, phosphonate, phosphate, quaternary ammonium and carboxyl; and n is an integer from 1 to 6.

In a first embodiment of the first aspect, the dye of formula (I) is a fluorescent dye wherein:

groups $R^3$ and $R^4$ are attached to atoms of the $Z^1$ ring structure and groups $R^5$ and $R^6$ are attached to atoms of the $Z^2$ ring structure, where $Z^1$ and $Z^2$ are hereinbefore defined;

$R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2—)_nY$; and $R^1$ and $R^2$ are independently selected from hydrogen, $C_1$-$C_{20}$ alkyl, aralkyl, the group -E-F and the group —$(CH_2—)_nY$; wherein E, F, Y and n are hereinbefore defined.

The quinacridone dyes according to the first embodiment of the first aspect are particularly suitable for use as fluorescence lifetime dyes. In the context of the present invention, the term lifetime dye is intended to mean a dye having a measurable fluorescence lifetime, defined as the average amount of time that the dye remains in its excited state following excitation (Lakowicz, J. R., Principles of Fluorescence Spectroscopy, Kluwer Academic/Plenum Publishers, New York, (1999)). Alternatively, the dyes may be used in assays utilising fluorescence polarisation.

Suitably, the fluorescent dyes according to the first embodiment of the first aspect exhibit a fluorescence lifetime in the range from 1 to 30 nanoseconds. Preferably, the fluorescent lifetimes of the dyes are in the range from 10 to 25 nanoseconds.

In a second embodiment of the first aspect, the dye of formula (I) is a non-fluorescent or substantially non-fluorescent dye wherein:

groups $R^1$, $R^2$, $R^3$, $R^4$, $R^5$, $R^6$, $R^7$, $R^8$, $Z^1$ and $Z^2$ are hereinbefore defined; and wherein at least one of groups $R^1$, $R^2$, $R^3$, $R^4$, $R^5$, $R^6$, $R^7$ and $R^8$ comprises at least one nitro group.

In this embodiment, suitably, the at least one nitro group may be attached directly to the $Z^1$ and/or $Z^2$ ring structures. In the alternative, a mono- or di-nitro-substituted benzyl group may be attached to the $R^1$, $R^2$, $R^3$, $R^4$, $R^5$, $R^6$, $R^7$ or $R^8$ positions, which optionally may be further substituted with one or more nitro groups attached directly to the $Z^1$ and/or $Z^2$ ring structures.

Preferably, in the first and second embodiments, at least one of groups $R^1$, $R^2$, $R^3$, $R^4$, $R^5$, $R^6$, $R^7$ and $R^8$ in the dye of formula (I) is the group -E-F where E and F are hereinbefore defined.

Suitably, the target bonding group F is a reactive or functional group. A reactive group of a dye of formula (I) can react under suitable conditions with a functional group of a target material; a functional group of a dye of formula (I) can react under suitable conditions with a reactive group of the target material such that the target material becomes labelled with the compound.

Preferably, when F is a reactive group, it is selected from succinimidyl ester, sulpho-succinimidyl ester, isothiocyanate, maleimide, haloacetamide, acid halide, vinylsulphone, dichlorotriazine, carbodiimide, hydrazide and phosphoramidite. Preferably, when F is a functional group, it is selected from hydroxy, amino, sulphydryl, imidazole, carbonyl including aldehyde and ketone, phosphate and thiophosphate. By virtue of these reactive and functional groups the dye of formula (I) may react with and covalently bond to target materials.

Suitably, $Z^1$ and $Z^2$ may be selected from the group consisting of phenyl, pyridinyl, naphthyl, anthranyl, indenyl, fluorenyl, quinolinyl, indolyl, benzothiophenyl, benzofuranyl and benzimidazolyl moieties. Additional one, two fused, or three fused ring structures will be readily apparent to the skilled person. Preferred $Z^1$ and $Z^2$ are selected from the group consisting of phenyl, pyridinyl, naphthyl, quinolinyl and indolyl moieties. Particularly preferred $Z^1$ and $Z^2$ are phenyl and naphthyl moieties.

Preferably, at least one of the groups $R^1$, $R^2$, $R^3$, $R^4$, $R^5$, $R^6$, $R^7$ and $R^8$ of the dyes of formula (I) is a water solubilising group for conferring a hydrophilic characteristic to the compound. Solubilising groups, for example, sulphonate, sulphonic acid and quaternary ammonium, may be attached directly to the aromatic ring structures $Z^1$ and/or $Z^2$ of the compound of formula (I). Alternatively, solubilising groups may be attached by means of a $C_1$ to $C_6$ alkyl linker chain to said aromatic ring structures and may be selected from the group —$(CH_2—)_nY$ where Y is selected from sulphonate, sulphate, phosphonate, phosphate, quaternary ammonium and carboxyl; and n is an integer from 1 to 6. Alternative solubilising groups may be carbohydrate residues, for example, monosaccharides. Examples of water solubilising constituents include $C_1$-$C_6$ alkyl sulphonates, such as —$(CH_2)_3$—$SO_3$— and —$(CH_2)_4$—$SO_3^-$. However, one or more sulphonate or sulphonic acid groups attached directly to the aromatic ring structures of a dye of formula (I) are particularly preferred. Water solubility may be advantageous when labelling proteins.

Suitable spacer groups E may contain 1-60 chain atoms selected from the group consisting of carbon, nitrogen, oxygen, sulphur and phosphorus. For example the spacer group may be:

—$(CHR')_p$—
—$\{(CHR')_q$—O—$(CHR')_r\}_s$—
—$\{(CHR')_q$—NR'—$(CHR')_r\}_s$—
—$\{(CHR')_q$—(CH=CH)—$(CHR')_r\}_s$—
—$\{(CHR')_q$—Ar—$(CHR')_r\}_s$—
—$\{(CHR')_q$—CO—NR'—$(CHR')_r\}_s$—
—$\{(CHR')_q$—CO—Ar—NR'—$(CHR')_r\}_s$— where R' is hydrogen, $C_1$-$C_4$ alkyl or aryl, which may be optionally substituted with sulphonate, Ar is phenylene, optionally substituted with sulphonate, p is 1-20, preferably 1-10, q is 0-10, r is 1-10 and s is 1-5.

Specific examples of reactive groups $R^1$, $R^2$, $R^3$, $R^4$, $R^5$, $R^6$, $R^7$ and $R^8$ and the groups with which $R^1$, $R^2$, $R^3$, $R^4$, $R^5$, $R^6$, $R^7$ and $R^8$ can react are provided in Table 1. In the alternative, groups $R^1$, $R^2$, $R^3$, $R^4$, $R^5$, $R^6$, $R^7$ and $R^8$ may be the functional groups of Table 1 which would react with the reactive groups of a target material.

TABLE 1

Possible Reactive Substituents and Sites Reactive Therewith

| Reactive Groups | Functional Groups |
|---|---|
| succinimidyl esters | primary amino, secondary amino |
| isothiocyanates | amino groups |
| haloacetamides, maleimides | sulphydryl, imidazole, hydroxyl, amine |
| acid halides | amino groups |
| anhydrides | primary amino, secondary amino, hydroxyl |
| hydrazides, | aldehydes, ketones |
| vinylsulphones | amino groups |
| dichlorotriazines | amino groups |
| carbodiimides | carboxyl groups |
| phosphoramidites | hydroxyl groups |

Preferred reactive groups which are especially useful for labelling target materials with available amino and hydroxyl functional groups include:

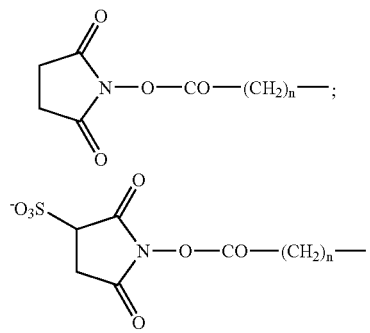

where n is 0 or an integer from 1-10.

Aryl is an aromatic substituent containing one or two fused aromatic rings containing 6 to 10 carbon atoms, for example phenyl or naphthyl, the aryl being optionally and independently substituted by one or more substituents, for example halogen, hydroxyl, straight or branched chain alkyl groups containing 1 to 10 carbon atoms, aralkyl and $C_1$-$C_6$ alkoxy, for example methoxy, ethoxy, propoxy and n-butoxy.

Heteroaryl is a mono- or bicyclic 5 to 10 membered aromatic ring system containing at least one and no more than 3 heteroatoms which may be selected from N, O, and S and is optionally and independently substituted by one or more substituents, for example halogen, hydroxyl, straight or branched chain alkyl groups containing 1 to 10 carbon atoms, aralkyl and $C_1$-$C_6$ alkoxy, for example methoxy, ethoxy, propoxy and n-butoxy.

Aralkyl is a $C_1$ to $C_6$ alkyl group substituted by an aryl or heteroaryl group.

Halogen and halo groups are selected from fluorine, chlorine, bromine and iodine.

Exemplary dyes according to the first embodiment of the first aspect are as follows:
i) 6-{2,9-dimethoxy-12-(5-carboxypentyl)-7,14-dioxo-7,14-dihydro-12H-quino[2,3-b]acridin-5-yl}hexanoic acid, diethyl ester;
ii) 6-{2,9-dibromo-12-(5-carboxypentyl)-7,14-dioxo-7,14-dihydro-12H-quino[2,3-b]acridin-5-yl}hexanoic acid;
iii) 6-{12-ethyl-7,14-dioxo-2,9-disulpho-7,14-dihydro-12H-quino[2,3-b]acridin-5-yl}hexanoic acid.

The fluorescent dyes according to the present invention may be used to label and thereby impart fluorescent properties to a variety of target biological materials. Thus, in a second aspect, there is provided a method for labelling a target biological material the method comprising:
i) adding to a liquid containing said target biological material a dye of formula (I):

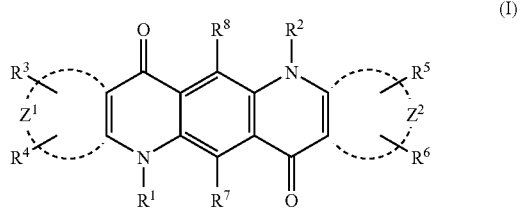

wherein:
groups $R^3$ and $R^4$ are attached to the $Z^1$ ring structure and groups $R^5$ and $R^6$ are attached to the $Z^2$ ring structure, where $Z^1$ and $Z^2$ are hereinbefore defined;
$R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2—)_nY$;
$R^1$ and $R^2$ are independently selected from hydrogen, $C_1$-$C_{20}$ alkyl, aralkyl, the group -E-F and the group —$(CH_2—)_nY$;
where E, F, Y and n are hereinbefore defined; and
ii) incubating said dye with said target biological material under conditions suitable for labelling said target.

Suitably, the fluorescent dyes of the present invention wherein at least one of the groups $R^1$ to $R^8$ contains a charge, for example, quaternary amino, may be used to bind non-covalently to charged biological molecules such as, for example, DNA and RNA. Alternatively, fluorescent dyes of the present invention wherein at least one of the groups $R^1$ to $R^8$ is an uncharged group, for example, a long chain alkyl, an aryl group, or an ester group may be used to bind to and thereby label uncharged biological molecules such as, for example, biological lipids, as well as to intact cell membranes, membrane fragments and cells.

In a preferred embodiment according to the second aspect, at least one of groups $R^1$, $R^2$, $R^3$, $R^4$, $R^5$, $R^6$, $R^7$ and $R^8$ in the dye of formula (I) is the group -E-F where E and F are hereinbefore defined. In this embodiment, the fluorescent dyes may be used to covalently label a target biological material. The target bonding group may be a reactive group for reacting with a functional group of the target material. Alternatively, the target bonding group may be a functional group for reacting with a reactive group on the target biological material. The method comprises incubating the target biological material with an amount of the dye according to the invention under conditions to form a covalent linkage between the target material and the dye. The target may be incubated with an amount of a compound according to the present invention having at least one of groups $R^1$, $R^2$, $R^3$, $R^4$, $R^5$, $R^6$, $R^7$ and $R^8$ that includes a reactive or functional group that can covalently bind with the functional or reactive group of the target biological material.

Suitable target biological materials include, but are not limited to the group consisting of antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, hormones, cells, cell membranes and toxins.

Fluorescent dyes according to the present invention may be used in assay methods that employ fluorescent labels for the detection and/or measurement of analytes using, for example, fluorescence intensity, fluorescence lifetime, or fluorescence polarisation measurements. Examples of such assays include protein-protein binding assays, immunoassays and nucleic acid hybridisation assays.

In a third aspect, there is provided a method for the assay of an analyte in a sample which method comprises:
i) contacting the analyte with a specific binding partner for said analyte under conditions suitable to cause the binding of at least a portion of said analyte to said specific binding partner to form a complex and wherein one of said analyte and said specific binding partner is labelled with a fluorescent dye of formula (I):

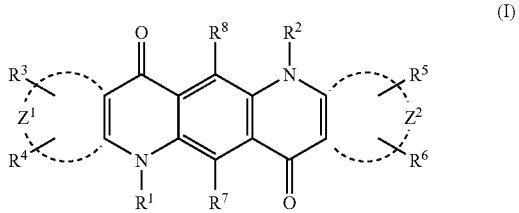

wherein:

groups $R^3$ and $R^4$ are attached to atoms of the $Z^1$ ring structure and groups $R^5$ and $R^6$ are attached to atoms of the $Z^2$ ring structure, where $Z^1$ and $Z^2$ are hereinbefore defined;

at least one of groups $R^1$, $R^2$, $R^3$, $R^4$, $R^5$, $R^6$, $R^7$ and $R^8$ is the group -E-F where E is a spacer group having a chain from 1-60 atoms selected from the group consisting of carbon, nitrogen, oxygen, sulphur and phosphorus atoms and F is a target bonding group;

when any of said groups $R^3$, $R^4$, $R^5$, $R^6$, $R^7$ and $R^8$ is not said group -E-F, said remaining groups $R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_8$ alkoxy, acrylate, vinyl, styryl, aryl, heteroaryl, $C_1$-$C_{20}$ alkyl, aralkyl, sulphonate, sulphonic acid, quaternary ammonium and the group —$(CH_2—)_n Y$; and, when any of groups $R^1$ and $R^2$ is not said group -E-F, said remaining groups $R^1$ and $R^2$ are independently selected from hydrogen, $C_1$-$C_{20}$ alkyl, aralkyl and the group —$(CH_2—)_n Y$;

wherein Y and n are hereinbefore defined;

ii) measuring the emitted fluorescence of the labelled complex; and iii) correlating the emitted fluorescence with the presence or the amount of said analyte in said sample.

Suitably, step ii) may be performed by measurement of the fluorescence intensity, fluorescence lifetime, or fluorescence polarisation of the labelled complex. Preferably, the measuring step ii) is performed by measuring the fluorescence lifetime, or the fluorescence polarisation of the labelled complex.

In one embodiment, the assay method is a direct assay for the measurement of an analyte in a sample. A known or putative inhibitor compound may be optionally included in the reaction mixture.

In a second, or alternative embodiment, the assay may be a competitive assay wherein a sample containing an analyte competes with a fluorescent tracer for a limited number of binding sites on a binding partner that is capable of specifically binding the analyte and the tracer. Suitably, the tracer is a labelled analyte or a labelled analyte analogue, in which the label is a fluorescent dye of formula (I). Increasing amounts (or concentrations) of the analyte in the sample will reduce the amount of the fluorescent labelled analyte or fluorescent labelled analyte analogue that is bound to the specific binding partner. The fluorescence signal is measured and the concentration of analyte may be obtained by interpolation from a standard curve.

In a further embodiment, the binding assay may employ a two-step format, wherein a first component (which may be optionally coupled to an insoluble support) is bound to a second component to form a specific binding complex, which is bound in turn to a third component. In this format, the third component is capable of specifically binding to either the second component, or to the specific binding complex. Either of the second or the third component may be labelled with a fluorescent dye according to the present invention. Examples include "sandwich" assays, in which one component of a specific binding pair, such as a first antibody, is coated onto a surface, such as the wells of a multiwell plate. Following the binding of an antigen to the first antibody, a fluorescent labelled second antibody is added to the assay mix, so as to bind with the antigen-first antibody complex. The fluorescence signal is measured and the concentration of antigen may be obtained by interpolation from a standard curve.

In particularly preferred embodiments, the measurement step may be performed using fluorescence polarisation. Thus, when the fluorescent tracer is not bound to the specific binding partner, it will tumble and reorientate rapidly relative to the fluorescence lifetime of the fluorescent dye. When bound to the specific binding partner, the tracer will tumble and reorientate slowly relative to the fluorescence lifetime of the dye. The degree of polarisation is therefore proportional to the extent of binding of the fluorescent tracer in the sample and inversely proportional to the amount of analyte in the sample.

Examples of analyte-specific binding partner pairs include, but are not restricted to, antibodies/antigens, lectins/glycoproteins, biotin/streptavidin, hormone/receptor, enzyme/substrate or co-factor, DNA/DNA, DNA/RNA and DNA/binding protein. It is to be understood that any molecules which possess a specific binding affinity for each other may be employed, so that the fluorescent dyes of the present invention may be used for labelling one component of a specific binding pair, which in turn may be used in the detection of binding to the other component.

The dyes according to the present invention may also be used in enzyme assays, utilising fluorescence polarisation measurements. An assay for the detection of enzyme activity may be configured as follows. A reaction mixture is prepared by combining the enzyme and a fluorogenic substrate labelled with a fluorescent dye according to the present invention. A known or putative inhibitor compound may be optionally included in the reaction mixture. The progress of the reaction may be monitored by observing a change in fluorescence polarisation of the sample.

Thus, in a fourth aspect, there is provided an assay method for the determination of an enzyme in a sample, the method comprising:

i) providing a substrate for the enzyme wherein the substrate is labelled with a fluorescent dye of formula (I):

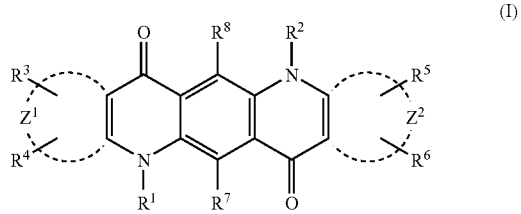

wherein:
groups $R^3$ and $R^4$ are attached to atoms of the $Z^1$ ring structure and groups $R^5$ and $R^6$ are attached to atoms of the $Z^2$ ring structure, where $Z^1$ and $Z^2$ are hereinbefore defined;
at least one of groups $R^1$, $R^2$, $R^3$, $R^4$, $R^5$, $R^6$, $R^7$ and $R^8$ is the group -E-F where E is a spacer group having a chain from 1-60 atoms selected from the group consisting of carbon, nitrogen, oxygen, sulphur and phosphorus atoms and F is a target bonding group;
when any of said groups $R^3$, $R^4$, $R^5$, $R^6$, $R^7$ and $R^8$ is not said group -E-F, said remaining groups $R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium and the group —$(CH_2$—$)_n Y$; and,
when any of groups $R^1$ and $R^2$ is not said group -E-F, said remaining groups $R^1$ and $R^2$ are independently selected from hydrogen, $C_1$-$C_{20}$ alkyl, aralkyl and the group —$(CH_2$—$)_n Y$;
wherein Y and n are hereinbefore defined;
ii) combining the labelled substrate with the enzyme under conditions suitable for initiating the enzymatic reaction; and
iii) measuring the fluorescence polarisation of the sample to determine the extent of reaction.

Suitably, the enzyme may be selected from cleavage enzymes such as proteases that catalyse cleavage of the substrate into two or more fragments, thereby resulting in a decrease in fluorescence polarisation. Alternatively the enzyme may join two components, for example, a ligase or a transferase, resulting in an increase in polarisation of the sample.

The fluorescent dyes according to the first embodiment of the first aspect may be used in applications that include detecting and distinguishing between various components in a mixture. In a fifth aspect, the present invention provides a set of two or more different fluorescent dyes, each dye of said set of dyes having the formula (I):

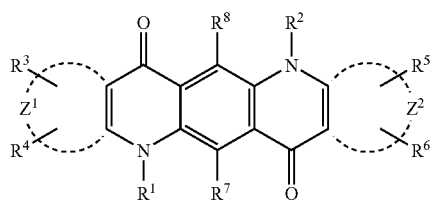

wherein:
groups $R^3$ and $R^4$ are attached to atoms of the $Z^1$ ring structure and groups $R^5$ and $R^6$ are attached to atoms of the $Z^2$ ring structure, where $Z^1$ and $Z^2$ are hereinbefore defined;
$R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2$—$)_n Y$;
$R^1$ and $R^2$ are independently selected from hydrogen, $C_1$-$C_{20}$ alkyl, aralkyl, the group -E-F and the group —$(CH_2$—$)_n Y$;

E is a spacer group having a chain from 1-60 atoms selected from the group consisting of carbon, nitrogen, oxygen, sulphur and phosphorus atoms and F is a target bonding group;
Y is selected from sulphonate, sulphate, phosphonate, phosphate, quaternary ammonium and carboxyl; and n is an integer from 1 to 6;
wherein each dye of said set has a distinguishably different fluorescence lifetime compared with the lifetimes of the remaining dyes of the set.

Preferably, in each dye of the set of dyes at least one of groups $R^1$, $R^2$, $R^3$, $R^4$, $R^5$, $R^6$, $R^7$ and $R^8$ is the group -E-F where E and F are hereinbefore defined.

Preferably, the set of fluorescent dyes according to the invention will comprise four different dyes, each dye of the set having a different fluorescence lifetime. Preferably, each of the fluorescent dyes of the set of dyes exhibits a fluorescence lifetime in the range from 1 to 30 nanoseconds, more preferably, in the range from 10 to 25 nanoseconds.

To distinguish between different fluorescent dyes in the set of dyes, the lifetime of the fluorescence emission of each of the dyes is preferably separated by at least 0.5 nanoseconds.

The set of dyes may be used in a detection method wherein different fluorescent dyes of the set of dyes are covalently bonded to a plurality of different primary components, each primary component being specific for a different secondary component, in order to identify each of a plurality of secondary components in a mixture of secondary components. The method comprises covalently binding different dyes of a set of fluorescent dyes according to the fifth aspect of the invention to different primary components in a multicomponent mixture wherein each dye of the set has a different fluorescence lifetime, compared with the fluorescence lifetimes of the remaining dyes of the set; adding the dye-labelled primary components to a preparation containing secondary components under conditions to enable binding of at least a portion of each of said dye-labelled primary components to its respective secondary component; and determining the presence or the amount of the bound secondary component by measuring the fluorescence lifetime of each of the labelled primary component-secondary component complexes.

If required, any unreacted primary components may be removed or separated from the preparation by, for example washing, to prevent interference with the analysis.

Preferably, a single wavelength of excitation can be used to excite fluorescence from two or more materials in a mixture, where each fluoresces having a different characteristic fluorescent lifetime.

The set of fluorescent dyes according to the present invention may be used in any system in which the creation of a fluorescent primary component is possible. For example, an appropriately reactive fluorescent dye according to the invention can be conjugated to a DNA or RNA fragment and the resultant conjugate then caused to bind to a complementary target strand of DNA or RNA. Other examples of primary component-secondary component complexes which may be detected include antibodies/antigens and biotin/streptavidin.

The set of fluorescent dyes according to the present invention may also be advantageously used in fluorescent DNA sequencing based upon fluorescence lifetime discrimination of the DNA fragments. Briefly, each one of a set of dyes, may be coupled to a primer. Various primers are available, such as primers from pUC/M13, λgt10, λgt11 and the like (see Sambrook et al, Molecular Cloning, A Laboratory Manual $2^{nd}$ Edition, Cold Spring Harbour Laboratory Press 1989). DNA sequences are cloned into an appropriate vector having a primer sequence joined to the DNA fragment to be sequenced. After hybridisation to the DNA template, polymerase enzyme-directed synthesis of a complementary strand occurs. Different 2',3'-dideoxynucleotide terminators are employed in each is different sequencing reaction so as to obtain base-specific termination of the chain extension reaction. The resulting set of DNA fragments are separated by electrophoresis and the terminating nucleotide (and thus the DNA sequence) is determined by detecting the fluorescence lifetime of the labelled fragments. DNA sequencing may also be performed using dideoxynucleotide terminators covalently labelled with the fluorescent dyes according to the present invention.

The non-fluorescent or substantially non-fluorescent dyes according to the second embodiment of the first aspect may be used as the substrate for an enzyme and which upon reaction with the enzyme, yields a fluorescent product.

Bacterial nitroreductases have been shown to catalyse the general reaction set out below in Reaction Scheme 1.

Reaction Scheme 1

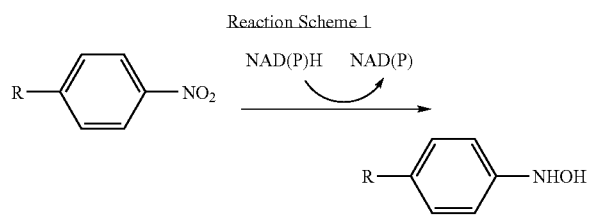

where, in the presence of NADH or NADPH, one or more nitro groups on an organic molecule may be reduced to a hydroxylamine (—NHOH) group which may subsequently be converted to an amine (—NH$_2$) group.

Thus, in a sixth aspect of the invention, there is provided a method of increasing the fluorescence of a non-fluorescent or substantially non-fluorescent dye of formula (I):

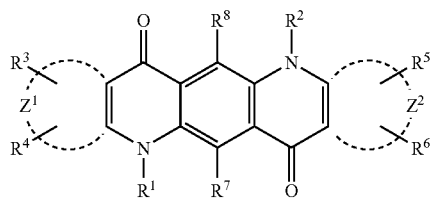

wherein:
groups $R^1$, $R^2$, $R^3$, $R^4$, $R^5$, $R^6$, $R^7$, $R^8$, $Z^1$ and $Z^2$ are hereinbefore defined; and wherein at least one of groups $R^1$, $R^2$, $R^3$, $R^4$, $R^5$, $R^6$, $R^7$ and $R^8$ comprises at least one nitro group;
characterised by the reduction of said at least one nitro group to —NHOH or —NH$_2$ Suitably, reduction is by means of nitroreductase. This can be achieved by enzymatic conversion of a nitro group in a compound of formula (I) to a —NHOH or —NH$_2$ group by the action of the nitroreductase. Depending on the structure of the dye, the intensity and/or lifetime of the fluorescence emission from the product of the nitroreductase reaction may be increased so as to exhibit a lifetime typically in the range from 1 to 30 nanoseconds. Moreover, the fluorescence lifetime characteristics of the reaction product can be altered to suit the application by means of additional substitutents, whilst retaining the nitro group(s) that are involved in the reaction with nitroreductase. Thus, fluorescent reporters compatible for use with other fluors in multiplex systems can be provided.

In a seventh aspect of the invention there is provided a method for detecting nitroreductase enzyme activity in a composition comprising:
i) mixing said composition under conditions to promote nitroreductase activity with a dye of formula (I):

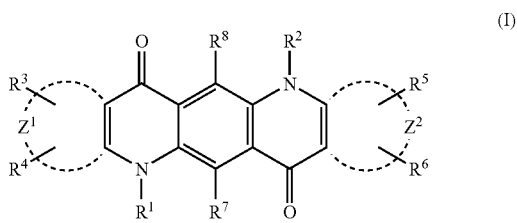

wherein:
groups $R^1$, $R^2$, $R^3$, $R^4$, $R^5$, $R^6$, $R^7$, $R^8$, $Z^1$ and $Z^2$ are hereinbefore defined and wherein at least one of groups $R^1$, $R^2$, $R^3$, $R^4$, $R^5$, $R^6$, $R^7$ and $R^8$ comprises at least one nitro group; and
ii) measuring an increase in fluorescence wherein said increase is a measure of the amount of nitroreductase activity.

Suitably, the measurement step (ii) may be a measure of fluorescence intensity and/or fluorescence lifetime of the labelled product of the nitroreductase reaction.

In one embodiment of the seventh aspect, the composition comprises a cell or cell extract. In principle, any type of cell can be used, i.e. prokaryotic or eukaryotic (including bacterial, mammalian and plant cells). Where appropriate, a cell extract can be prepared from a cell, using standard methods known to those skilled in the art (Molecular Cloning, A Laboratory Manual 2$^{nd}$ Edition (1989), Cold Spring Harbour Laboratory Press), prior to measuring fluorescence.

Typical conditions for nitroreductase activity comprise incubation of the composition in a suitable medium and the dye at approximately 37° C. in the presence of NADH and FMN.

In a eighth aspect of the invention there is provided an assay method comprising:
i) binding one component of a specific binding pair to a surface;
ii) adding a second component of the specific binding pair under conditions to promote binding between the components, said second component being labelled with a nitroreductase enzyme;
iii) adding a dye of formula (I):

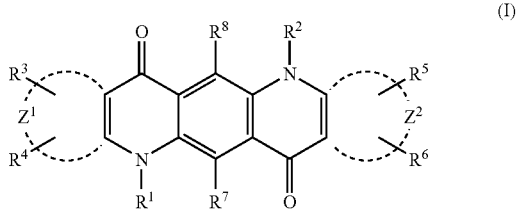

wherein:

groups $R^1$, $R^2$, $R^3$, $R^4$, $R^5$, $R^6$, $R^7$, $R^8$, $Z^1$ and $Z^2$ are hereinbefore defined and wherein at least one of groups $R^1$, $R^2$, $R^3$, $R^4$, $R^5$, $R^6$, $R^7$ and $R^8$ comprises at least one nitro group; and iv) detecting binding of the second component to the first component by measuring an increase in fluorescence as a measure of bound nitroreductase activity.

In a preferred embodiment of the eighth aspect, said specific binding pair is selected from the group consisting of antibodies/antigens, lectins/glycoproteins, biotin/streptavidin, hormone/receptor, enzyme/substrate, DNA/DNA, DNA/RNA and DNA/binding protein.

Briefly, an in vitro assay method for the detection of antibody binding may be configured as follows. An antibody specific for an antigen of interest may be labelled by covalently linking it to an enzymatically active nitroreductase. The labelled antibody can then be introduced into the test sample containing the antigen under binding conditions. After washing to remove any unbound antibody, the amount of bound antibody is detected by incubating the sample with a substrate comprising a compound of formula (I) having at least one nitro group under conditions promoting nitroreductase activity and measuring an increase in fluorescence. The amount of fluorescence detected will be proportional to the amount of nitroreductase-labelled antibody that has bound to the analyte.

In an in vitro assay for detecting the binding of nucleic acids by hybridisation, either of the pair of target and probe nucleic acid is bound to a membrane or surface. The unbound partner is labelled with nitroreductase and incubated under hybridising conditions with the bound nucleic acid. Unbound, labelled nucleic acid is washed off and the amount of bound, labelled nucleic acid is measured by incubating the membrane or surface with a compound of formula (I) having at least one nitro group under conditions suitable for nitroreductase activity. The amount of increase in fluorescence gives a measure of the amount of bound labelled DNA.

Methods for coupling enzymes, such as nitroreductase, to other biomolecules, e.g. proteins and nucleic acids, are well known (Bioconjugate Techniques, Academic Press 1996). Coupling may be achieved by direct means, for example by use of a suitable bifunctional crosslinking agent (e.g. N-[γ-maleimidopropionic acid]hydrazine, Pierce) to covalently link the enzyme and binding partner. Alternatively, coupling may be achieved by indirect means, for example by separately biotinylating the enzyme and the binding partner using a chemically reactive biotin derivative, (e.g. N-hydroxysuccinimido-biotin, Pierce) and subsequently coupling the molecules through a streptavidin bridging molecule.

Cell based assays are increasingly attractive over in vitro biochemical assays for use in high throughput screening (HTS). This is because cell based assays require minimal manipulation and the readouts can be examined in a biological context that more faithfully mimics the normal physiological situation. Such in vivo assays require an ability to measure a cellular process and a means to measure its output. For example, a change in the pattern of transcription of a number of genes can be induced by cellular signals triggered, for example, by the interaction of an agonist with its cell surface receptor or by internal cellular events such as DNA damage. The induced changes in transcription can be identified by fusing a reporter gene to a promoter region which is known to be responsive to the specific activation signal.

In fluorescence-based enzyme-substrate systems, an increase in fluorescence gives a measure of the activation of the expression of the reporter gene.

Accordingly, in a ninth aspect of the invention, there is provided an assay method which comprises:

i) contacting a host cell which has been transfected with a nucleic acid molecule comprising expression control sequences operably linked to a sequence encoding a nitroreductase with a dye of formula (I):

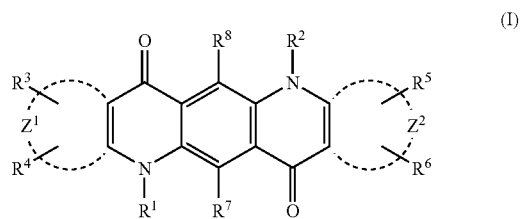

wherein:

groups $R^1$, $R^2$, $R^3{}_1$, $R^4$, $R^5$, $R^6{}_1$, $R^7$, $R^8$, $Z^1$ and $Z^2$ are hereinbefore defined and wherein at least one of groups $R^1$, $R^2$, $R^3$, $R^4$, $R^5$, $R^6$, $R^7$ and $R^8$ comprises at least one nitro group; and ii) measuring an increase in fluorescence as a measure of nitroreductase gene expression.

Suitably, the measurement step (ii) may be a measure of fluorescence intensity and/or fluorescence lifetime of the labelled product of the nitroreductase reaction.

In one embodiment of the ninth aspect, the assay method is conducted in the presence of a test agent whose effect on gene expression is to be determined.

Methods for using a variety of enzyme genes as reporter genes in mammalian cells are well known (for review see Naylor L. H., Biochemical Pharmacology, (1999), 58, 749-757). The reporter gene is chosen to allow the product of the gene to be measurable in the presence of other cellular proteins and is introduced into the cell under the control of a chosen regulatory sequence which is responsive to changes in gene expression in the host cell. Typical regulatory sequences include those responsive to hormones, second messengers and other cellular control and signalling factors. For example, agonist binding to seven transmembrane receptors is known to modulate promoter elements including the cAMP responsive element, NF-AT, SRE and AP1; MAP kinase activation leads to modulation of SRE leading to Fos and Jun transcription; DNA damage leads to activation of transcription of DNA repair enzymes and the tumour suppressor gene p53. By selection of an appropriate regulatory sequence the reporter gene can be used to assay the effect of added agents on cellular processes involving the chosen regulatory sequence under study.

For use as a reporter gene, the nitroreductase gene may be isolated by well known methods, for example by amplification from a cDNA library by use of the polymerase chain reaction (PCR) (Molecular Cloning, A Laboratory Manual $2^{nd}$ Edition, Cold Spring Harbour Laboratory Press (1989), pp 14.5-14.20). Once isolated, the nitroreductase gene may be inserted into a vector suitable for use with mammalian promoters (Molecular Cloning, A Laboratory Manual $2^{nd}$ Edition, Cold Spring Harbour Laboratory Press (1989), pp 16.56-16.57) in conjunction with and under the control of the gene regulatory sequence under study. The vector containing the nitroreductase reporter and associated regulatory sequences may then be introduced into the host cell by transfection using well known techniques, for example by use of DEAE-Dextran or Calcium Phosphate (Molecular Cloning, A Laboratory Manual 2$^{nd}$ Edition, Cold Spring Harbour Laboratory Press (1989), pp 16.30-16.46). Other suitable techniques will be well known to those skilled in the art.

In another embodiment of the ninth aspect, the dye of formula (I) wherein groups $R^1$, $R^2$, $R^3$, $R^4$, $R^5$, $R^6$, $R^7$, $R^8$, $Z^1$ and $Z^2$ are hereinbefore defined and wherein at least one of groups $R^1$, $R^2$, $R^3$, $R^4$, $R^5$, $R^6$, $R^7$ and $R^8$ comprises at least one nitro group, is permeable to cells. In this embodiment, preferably, at least one of groups $R^1$, $R^2$, $R^3$, $R^4$, $R^5$, $R^6$, $R^7$ and $R^8$ comprises a cell membrane permeabilising group. Membrane permeant compounds can be generated by masking hydrophilic groups to provide more hydrophobic compounds. The masking groups can be designed to be cleaved from the substrate within the cell to generate the derived fluorogenic substrate intracellularly. Because the substrate is more hydrophilic than the membrane permeant derivative, it is then trapped in the cell. Suitable cell membrane permeabilising groups may be selected from acetoxymethyl ester, which is readily cleaved by endogenous mammalian intracellular esterases (Jansen, A. B. A. and Russell, T. J., J.Chem.Soc., (1965), 2127-2132 and Daehne W. et al. J.Med.Chem., (1970) 13, 697-612) and pivaloyl ester (Madhu et al., J. Ocul.Pharmacol.Ther., (1998), 14(5), 389-399) although other suitable groups will be recognised by those skilled in the art.

Typically, to assay the activity of a test agent to activate cellular responses via the regulatory sequence under study, cells transfected with the nitroreductase reporter are incubated with the test agent, followed by addition of a dye of formula (I) wherein at least one of groups $R^1$, $R^2$, $R^3$, $R^4$ and $R^5$ in said dye comprises at least one nitro group, said compound being made cell permeant. After an appropriate period required for conversion of the substrate to a form exhibiting fluorescence characteristics, the fluorescence intensity and/or fluorescence lifetime from the cells is measured at an emission wavelength appropriate for the chosen dye. Measurement of fluorescence may be readily achieved by use of a range of detection instruments including fluorescence microscopes (e.g. LSM 410, Zeiss), microplate readers (e.g. CytoFluor 4000, Perkin Elmer), CCD imaging systems (e.g. LEADseeker™, Amersham Pharmacia Biotech) and Flow Cytometers (e.g. FACScalibur, Becton Dickinson).

The measured fluorescence is compared with fluorescence from control cells not exposed to the test agent and the effects, if any, of the test agent on gene expression modulated through the regulatory sequence, is determined from the ratio of fluorescence in the test cells to the fluorescence in the control cells. Where appropriate, a cell extract can be prepared using conventional methods.

Suitable means for expressing a nitroreductase enzyme include an expression plasmid or other expression construct. Methods for preparing such expression constructs are well known to those skilled in the art.

In a tenth aspect of the present invention, there is provided a dye of formula (I):

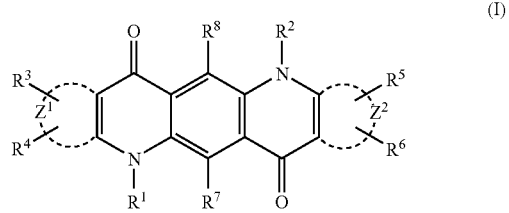

wherein:
groups $R^3$ and $R^4$ are attached to atoms of the $Z^1$ ring structure and groups $R^5$ and $R^6$ are attached to atoms of the $Z^2$ ring structure;
$Z^1$ and $Z^2$ independently represent the atoms necessary to complete one ring, two fused ring, or three fused ring aromatic or heteroaromatic systems, each ring having five or six atoms selected from carbon atoms and optionally no more than two atoms selected from oxygen, nitrogen and sulphur;
at least one of groups $R^1$, $R^2$, $R^3$, $R^4$, $R^5$, $R^6$, $R^7$ and $R^8$ is the group -E-F where E is a spacer group having a chain from 1-60 atoms selected from the group consisting of carbon, nitrogen, oxygen, sulphur and phosphorus atoms and F is a target bonding group; and,
when any of said groups $R^3$, $R^4$, $R^5$, $R^6$, $R^7$ and $R^8$ is not said group -E-F, said remaining groups $R^3$, $R^4$, $R^5$, $R^6$, $R^7$ and $R^8$ are independently selected from hydrogen, halogen, amide, hydroxyl, cyano, nitro, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium and the group —$(CH_2$—$)_n Y$; and,
when any of groups $R^1$ and $R^2$ is not said group -E-F, said remaining groups $R^1$ and $R^2$ are independently selected from hydrogen, mono- or di-nitro-substituted benzyl, $C_1$-$C_{20}$ alkyl, aralkyl and the group —$(CH_2$—$)_n Y$;
E is a spacer group having a chain from 1-60 atoms selected from the group consisting of carbon, nitrogen, oxygen, sulphur and phosphorus atoms and F is a target bonding group;
Y is selected from sulphonate, sulphate, phosphonate, phosphate, quaternary ammonium and carboxyl; and n is an integer from 1 to 6;
provided that at least one of groups $R^1$, $R^2$, $R^3$, $R^4$, $R^5$, $R^6$, $R^7$ and $R^8$ is a water solubilising group.

Preferably, the target bonding group F comprises a reactive group for reacting with a functional group on a target material, or a functional group for reacting with a reactive group on a target material. Preferred reactive groups may be selected from carboxyl, succinimidyl ester, sulpho-succinimidyl ester, isothiocyanate, maleimide, haloacetamide, acid halide, hydrazide, vinylsulphone, dichlorotriazine and phosphoramidite. Preferred functional groups may be selected from hydroxy, amino, sulphydryl, imidazole, carbonyl including aldehyde and ketone, phosphate and thiophosphate.

Preferably, the spacer group E is selected from:
—$(CHR')_p$—
—$\{(CHR')_q$—O—$(CHR')_r\}_s$—
—$\{(CHR')_q$—NR'—$(CHR')_r\}_s$—
—$\{(CHR')_q$—$(CH=CH)$—$(CHR')_r\}_s$—
—$\{(CHR')_q$—Ar—$(CHR')_r\}_s$—
—$\{(CHR')_q$—CO—NR'—$(CHR')_r\}_s$—
—$\{(CHR')_q$—CO—Ar—NR'—$(CHR')_r\}_s$— where R' is hydrogen, $C_1$-$C_4$ alkyl or aryl, which may be optionally substituted with sulphonate, Ar is phenylene, optionally substituted with sulphonate, p is 1-20, preferably 1-10, q is 0-10, r is 1-10 and s is 1-5.

Dyes according to the tenth aspect may contain a polymerizable group suitable for the formation of a polymer containing the dye. Suitable polymerizable groups are selected from acrylate, methacrylate and acrylamide. Polymerization may be carried out with a suitably derivatized compound of this invention used in conjunction with a second polymerizable monomer starting material, such as styrene or vinyltoluene, to form a copolymer containing the dye. The dyes of the present invention need not have a polymerisable group, for example, the dye may be incorporated during polymerisation or particle formation or may be absorbed into or onto polymer particles.

The dyes of formula (I) may be prepared by a process comprising reacting diethyl succinyl-succinate with an appropriately substituted aniline according to published methods (see Jaffe, E. E. and Marshall, W. J., U.S. Pat. No. 3,386,843; Jaffe, E. E. and Ehrich, F. F. U.S. Pat. No. 3,873,548). For example, heating diethyl succinyl-succinate with 4-aminobenzoic acid affords diethyl-2,5-di(4-carboxyanilino)-3,6-dihydroterphthalate. Further heating in a high boiling solvent affords 2,9-dicarboxy-6,13-dihydroquinacridone. Oxidation with sodium 3-nitrobenzene sulphonate gives 2,9-dicarboxyquinacridone. Alternative methods of synthesising quinacridone and its derivatives are disclosed by Bender, H. et al (U.S. Pat. No. 4,956,464), whereby 2,5-dianilino-3,6-dihydroterephthalic acid derivatives may be cyclized and dehydrogenated at 500-600° C. Maki, H. et al (U.S. Pat. No. 5,659,036) describe methods for preparing quinacridone derivatives in which alkyl esters of 1,4-cyclohexadione-2,5-dicarboxylic acid may be reacted with an appropriately substituted aromatic amine and the resultant 2,5-di(arylamino)-3,6-dihydroterephthalic acid dialkyl ester derivative may be cyclized to a 6,13-dihydroquinacridone which is then oxidized with a nitrobenzene sulphonic acid to give the quinacridone.

It will be readily appreciated that certain dyes of formula (I) may be useful as intermediates for conversion to other dyes of formula (I) by methods well known to those skilled in the art. Likewise, certain of the intermediates may be useful for the synthesis of dyes of formula (I). The compounds of the present invention may be synthesized by the methods disclosed herein. Derivatives of the dyes having a particular utility are prepared either by selecting appropriate precursors or by modifying the resultant compounds by known methods to include functional groups at a variety of positions. As examples, the dyes of the present invention may be modified to include certain reactive groups for preparing a fluorescent labelling reagent, or charged or polar groups may be added to enhance the solubility of the compound in polar or non-polar solvents or materials. As examples of conversions an ester may be converted to a carboxylic acid or may be converted to an amido derivative. Groups $R^1$ to $R^8$ may be chosen so that the compounds of the present invention have different fluorescence characteristics, thereby providing a number of related dyes which can be used in multiparameter analyses wherein the presence and quantity of different compounds in a single sample may be differentiated based on the wavelengths and lifetimes of a number of detected fluorescence emissions. The dyes of the present invention may be made soluble in aqueous, other polar, or non-polar media containing the material to be labelled by appropriate selection of R-groups.

The invention is further illustrated by reference to the following examples and figures in which.

Figure 1:
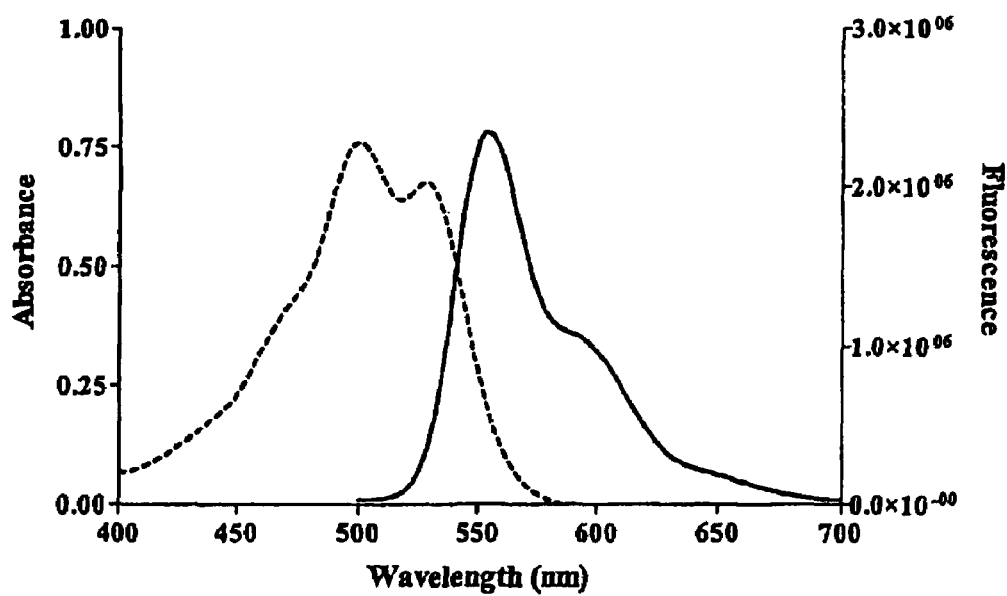
FIG. 1 is a plot showing the absorbance and emission spectrum of 6-{7,14-dioxo-2,9-disulpho-7,14-dihydro-12H-quino[2,3-b]acridin-5-yl}hexanoic acid.

Cy™ and LEADseeker™ are trademarks of Amersham Pharmacia Biotech UK Limited.

EXAMPLES 1. 2-Bromo-5,12-dihexylquinacridone (A) and 2,9-dibromo-5,12-dihexylquinacridone (B)

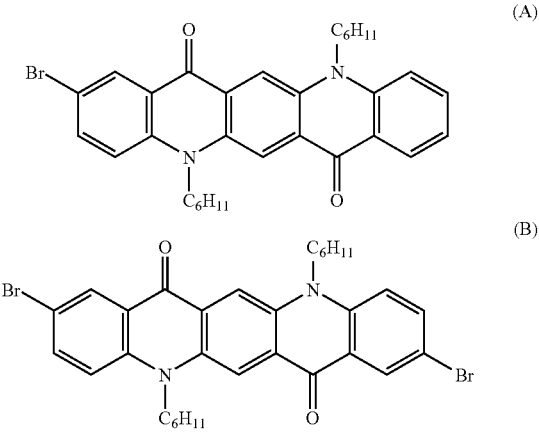

1.1 5,12-Dihexylquinacridone

A 25 ml RB flask was charged with quinacridone (Dojindo;156 mg, 0.5 mmol) and anhydrous N,N-dimethylformamide (5 ml). The flask was purged with nitrogen and set stirring. To the mixture was added sodium hydride (60 wt % dispersion in oil, 48 mg, 1.2 mmol) and the mixture left to stir. A blue colour slowly developed in the liquid phase but much of the solids remained undissolved after 2 hrs; dissolution was achieved by the addition of dimethyl sulphoxide (3 ml) to give a deep blue solution after a further 1 hr. At this point 1-iodohexane (295 μl, 2.0 mmol) was added and the mixture left to stir for 3 days. During this time the blue colour was completely discharged and an orange solid precipitated.

The mixture was quenched into 0.5M aqueous hydrochloric acid, the solid collected by filtration and washed with excess water. The damp solid was then dried by dissolution into dichloromethane containing anhydrous magnesium sulfate; the slurry was filtered and the brown-orange filtrate evaporated under vacuum to give the crude product. This was purified by flash chromatography (silica. 0-2.5% ethyl acetate in dichloromethane); pure fractions were pooled, filtered and evaporated, then triturated with diethyl ether to give an orange powder. Yield=161 mg (67%). $\lambda_{max}$ (CH$_2$Cl$_2$) =526, 493 nm. $\delta_H$ (200 MHz, CDCl$_3$) 0.95 (6H, t), 1.20-1.65 (12H, m), 2.01 (4H, m), 4.52 (4H, app t), 7.28 (2H, app t), 7.52 (2H, app d), 7.76 (2H, td), 8.58 (2H, dd) and 8.79 (2H, s).

Mass spectrum: (ES+) 481 (M+H), 503 (M+Na). Accurate mass: (M+H)=C$_{32}$H$_{37}$N$_2$O$_2$, requires 481.2855. Found 481.2844 (−2.3 ppm).

1.2 2-Bromo-5,12-dihexylquinacridone and 2,9-dibromo-5,12-dihexylquinacridone 5,12-Dihexylquinacridone (60 mg, 125 µmol) was mixed with ethanol (2.5 ml) and benzyltrimethylammonium tribromide (97 mg, 250 µmol). The resulting slurry was stirred at ambient temperature for 24 hrs, then heated under reflux for 16 hrs to give limited reaction. Addition of chloroform (2.5 ml) dissolved all solids to give an orange solution, continued reflux gave moderate generation of mono- and di-brominated products. After evaporation of solvent the products were isolated by flash chromatography (silica, dichloromethane) to give pure samples.

2-Bromo-5,12-dihexylquinacridone (A): $\lambda_{max}$ (CH$_2$Cl$_2$) =526, 493 nm. $\delta_H$ (200 MHz, CDCl$_3$) 0.95 (6H, m), 1.3-1.7 (12H, m), 1.9-2.1 (4H, m), 4.4-4.5 (4H, m), 7.25 (1H, m), 7.36 (1H, d), 7.48 (1H, d), 7.70-7.80 (2H, m), 8.52 (1H, dd), 8.61 (1H, s), 8.67 (1H, s) and 8.71 (1H, s). Mass spectrum (DEI+): 558+560 (ratio 1:1) (M+).

2,9-Dibromo-5,12-dihexylquinacridone (B): $\lambda_{max}$ (CH$_2$Cl$_2$)=532, 498 nm. $\delta_H$ (200 MHz, CDCl$_3$) 0.95 (6H, t), 1.3-1.7 (12H, m), 1.8-2.0 (4H, m), 4.5 (4H, t), 7.36 (2H, d), 7.78 (2H, dd), 8.58 (2H, d) and 8.64 (2H, s). Mass spectrum (DEI+): 636+638+640 (ratio 1:2:1) (M+).

2. Quinacridone-2,9-disulphonic acid, (di-potassium salt)

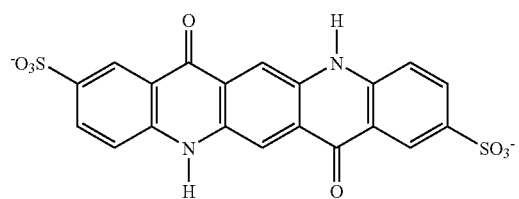

Quinacridone (200 mg, 0.645 mM) was placed in a round bottomed flask fitted with a magnetic stirrer and air condenser. The solid was dissolved in 98% sulphuric acid (2 ml) and heated to 110° C. for 6 hr under a nitrogen atmosphere. TLC (RP C-18 50/50 methanol/water) showed that all the starting material had been converted to a single fast moving component (visualised under long wavelength uv light). The reaction was dripped onto 10 ml ice to give a dark red solution. This was neutralised with solid potassium hydrogen carbonate to give a dark red precipitate. This was collected by centrifugation and the supernatant discarded.

Recrystallisation from water gave 0.21 g (0.386 Mm, 60%) of red solid identified as the di-potassium salt of quinacridone-2,9-disulphonic acid. Mass Spec(ES+). MH$^+$ 473.1; MK$_2^+$ 550.5. MPt >300° C.

$\lambda_{max}$(ab) 499, 527 nm (water); $\lambda_{max}$(em) 560,590 nm (water).

3. Quinacridone-2,4,9,11-tetrasulphonic acid (tetra-potassium salt)

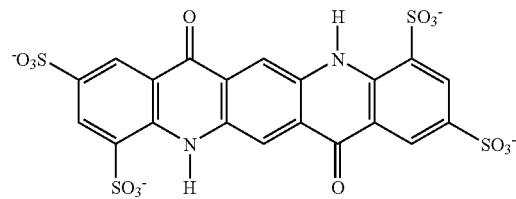

Quinacridone (500 mg, 1.61 mM) was placed in a round bottomed flask fitted with a magnetic stirrer and air condenser. The solid was dissolved in 20% oleum (5 mL) and heated to 110° C. for 20 hr under a nitrogen atmosphere. TLC (RP C-18 50/50 methanol/water) showed that all the starting material had been converted to a major fast moving component with two minor faster moving and one minor slower moving component (visualised under long wavelength uv light). The reaction was dripped onto 10 ml ice to give a dark red solution. This was neutralised with solid potassium hydrogen carbonate to give an orange precipitate. This was collected by centrifugation and the supernatant discarded.

Recrystallisation twice from water gave 1.1 gm of an orange solid identified as the tetra-potassium salt of quinacridone-2,4,9,11-tetrasulphonic acid. Mass Spec (ES+). MH$^+$ 632.9.

NMR (200 MHz, D$_2$O): δ 8.94 (doublet), δ 8.81 (single) δ 8.63 (doublet) 1:1:1. MPt >300° C. $\lambda_{max}$(ab) 499,527 nm (water); $\lambda_{max}$(em) 552 nm (water).

4. O—(N-Succinimidyl)-6-{7,14-dioxo-2,9-disulpho-7,14-dihydro-12H-quino[2,3-b]acridin-5-yl}hexanoate

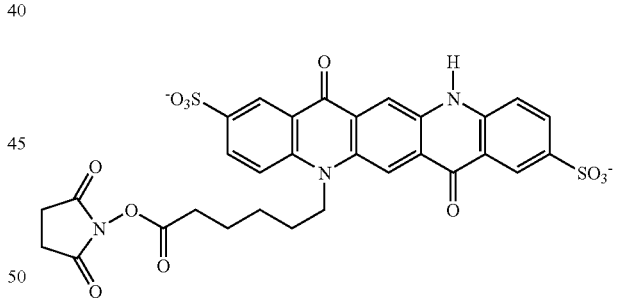

4.1 6-{7,14-Dioxo-2,9-disulpho-7,14-dihydro-12H-quino[2,3-b]acridin-5-yl}hexanoic acid ethyl ester Quinacridone-2,9-disulphonic acid (200 mg) was dried by repeated rotary evaporation with dry DMF. The material was then dissolved in 10 ml dry DMSO to give an orange solution. Potassium t-butoxide (45 mg, 0.4 mM) was added, the solution immediately turned blue. The solution was then stirred magnetically for 30 mins and then ethyl 6-bromohexanoate (70 µl, 0.4 mM) was added and the solution stirred under a nitrogen atmosphere for a further 24 hours. TLC (RP C-18 50/50 methanol/water) showed that approximately half of the starting material had been converted to a slightly slower running component. Further reaction time did not increase the amount of product. Mass spec. showed a peak at 692 corresponding to $MK_2^+$ for the required product. A further peak at 550 corresponds to $MK_2^+$ for the starting material. The solvent was removed by rotary evaporation to leave a red solid. No further attempt was made to purify this material which was used as such in subsequent reactions.

4.2 6-{7,14-Dioxo-2,9-disulpho-7,14-dihydro-12H-quino[2,3-b]acridin-5-yl}hexanoic acid The material from the above reaction was dissolved in 8 ml of a mixture of 1M hydrochloric acid: glacial acetic acid (1:3) and heated at 100° C. for two hours in a flask fitted with a reflux condenser and under a nitrogen atmosphere. Mass spec. showed the disappearance of the peak at 692 as described in the previous example and the appearance of a peak at 664 corresponding to $MK_2^+$ for 6-(7,14-dioxo-2,9-disulpho-7,14-dihydro-12H-quino[2,3-b]acridin-5-yl)hexanoic acid. A further peak at 550 corresponds to $MK_2^+$ for quinacridone-2,9-disulphonic acid. TLC (as described above showed a single spot). The solvents were removed by rotary evaporation to give a red solid. No attempt was made to purify this material which was then used in the next reaction.

4.3 O—(N-Succinimidyl)-6-{7,14-dioxo-2,9-disulpho-7,14-dihydro-12H-quino[2,3-b]acridin-5-yl}hexanoate The material from the previous reaction was dried by repeated rotary evaporation from DMF. The solid was then dissolved in 10 ml dry DMSO and 200 µl diisopropylethylamine was added followed by O-(succinimidyl)-N,N,N',N'-tetramethylene uronium hexafluorophosphate (HSPyU, 85 mg). The mixture was stirred at ambient temperature under a nitrogen atmosphere for 2 hrs. TLC (as described above) showed the presence of two spots. Mass spec. showed the disappearance of the peak at 692 as described in the previous example and the appearance of a peak at 684 corresponding to $MH^+$ for O—(N-succinimidyl)-6-{7,14-dioxo-2,9-disulpho-7,14-dihydro-12H-quino[2,3-b]acridin-5-yl}hexanoate. A further peak at 550 corresponds to $MK_2^+$ for quinacridone-2,9-disulphonic acid. The solvent was removed by rotary evaporation to leave a red gum. Trituration with ethyl acetate gave 74 mg of a red solid.

5. O—{N-succinimidyl-6-(12-ethyl-7,14-dioxo-2,9-disulpho-7,14-dihydro-12H-quino[2,3-b]acridin-5-yl}hexanoate

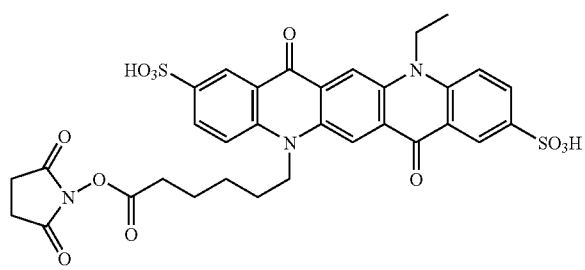

5.1 6-{12-ethyl-7,14-dioxo-7,14-dihydro-12H-quino[2,3-b]acridin-5-yl}hexanoic acid, ethyl ester Quinacridone (1.56 gm; 5.0 mmol) was suspended in anhydrous dimethylformamide (15 ml) and anhydrous dimethyl sulphoxide (15 ml) under a nitrogen atmosphere. Sodium hydride (60% suspension in oil; 240 mg; 6.0 mmol) was added and the mixture stirred until effervescence stopped. More sodium hydride (240 mg; 6.0 mmol) was added and the mixture stirred for 10 minutes when effervescence had ceased. The reaction was heated to 60° C. for 1 hour. Ethyl 6-bromohexanoate (890 µl; 5.0 mmol) was added to the dark green solution and the mixture stirred overnight at 60° C. Iodoethane (1.0 ml; 12.5 mmol) was then added and the mixture stirred for 2 hours at 60° C. The dark orange-red solution was allowed to cool, then the mixture was poured into water (300 ml). The solid was filtered off, washed with water and air dried. The solid was then dissolved in dichloromethane (300 ml) and anhydrous magnesium sulphate added. The mixture was filtered and the solvent removed by rotary evaporation to give a red solid. This was purified by flash chromatography (silica, 15% ethyl acetate/dichloromethane) to give 1.04 gm (43%) of the diethyl ester of 6-{12-ethyl-7,14-dioxo-7,14-dihydro-12H-quino[2,3-b]acridin-5-yl}hexanoic acid.

5.2 6-{12-ethyl-7,14-dioxo-2,9-disulpho-7,14-dihydro-12H-quino[2,3-b]acridin-5-yl}hexanoic acid The diethyl ester of 6-{12-ethyl-7,14-dioxo-7,14-dihydro-12H-quino[2,3-b]acridin-5-yl}hexanoic acid (241 mg; 0.5 mmol) was dissolved in conc. sulphuric acid (5 ml) and the purple solution heated at 110° C. overnight under an atmosphere of nitrogen. The reaction was allowed to cool and then poured onto ice (~20 gm). The solution was neutralised with 40% w/v sodium hydroxide solution to give a bright red solution. This was acidified with glacial acetic acid when a orange-red precipitate formed. This was collected by centrifugation, then dissolved in 0.1% trifluoroacetic acid (TFA) in water. The solution was purified by reverse phase HPLC. Vydac C18 semi-preparative column, water to acetonitrile gradient (both containing 0.1% v/v TFA), flow 5 ml/minute, detection at 530 nm. Purified material was pooled, evaporated to dryness under vacuum and then dried under vacuum over phosphorous pentoxide to give 300 mg (97%) of 6-{12-ethyl-7,14-dioxo-2,9-disulpho-7,14-dihydro-12H-quino[2,3-b]acridin-5-yl}hexanoic acid as a dark red solid.

$\delta_H$ (200 MHz, $CD_3OD$ +$D_2O$) 1.48(3H, t), 1.8(6H, m), 2.38(2H, m), 4.52(4H, m), 7.59(2H, m), 8.10(2H, d), 8.60 (2H, m), 8.89(2H, d). Accurate mass: (M+H) =$C_{28}H_{27}N_2O_{10}S_2$, requires 615.1107. Found 615.1089 (2.9 ppm). $\lambda_{max}$(ab) 294 nm ($\epsilon$=65,800/$M^{-1}cm^{-1}$); 506 nm ($\epsilon s$=5590/$M^{-1}cm^{-1}$); 536 nm ($\epsilon$=4790/$M^{-1}cm^{-1}$). (PBS buffer) $\lambda_{max}$(em) 563 nm (PBS buffer)

5.3 O—{N-Succinimidyl-6-(12-ethyl-7,14-dioxo-2,9-disulpho-7,14-dihydro-12H-quino[2,3-b]acridin-5-yl}hexanoate.

6-{12-Ethyl-7,14-dioxo-2,9-disulpho-7,14-dihydro-12H-quino[2,3-b]acridin-5-yl}hexanoic acid (15 mg; 241 µmol), O—(N-succinimidyl)-N,N,N',N'-tetramethyluronium tetrafluoroborate (8 mg; 27 µmol), anhydrous dimethyl sulphoxide (500 µl) and diisopropylethylamine (17.5 µl) were mixed to give an orange solution. This was left for 30 minutes when TLC ($RP_{18}$ 30:70 water:methanol) showed that the starting material had been converted to a slower running component identified as O—(N-succinimidyl-6-{12-ethyl-7,14-dioxo-2,9-disulpho-7,14-dihydro-12H-quino[2,3-b]acridin-5-yl}hexanoate by mass spectroscopy.

Mass spectrum: (ES+) (M+H) 712

6. 6-{2,9-Dibromo-12-(5-carboxypentyl)-7,14-dioxo-7,14-dihydro-12H-quino[2,3-b]acridin-5-yl}hexanoic acid

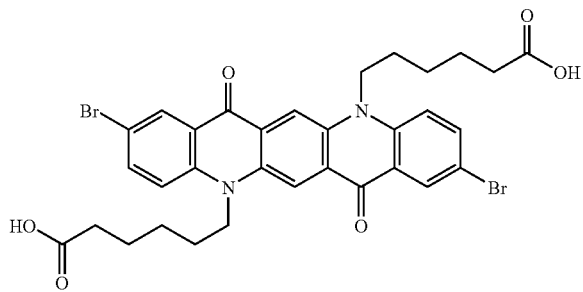

6.1 Dimethyl 2,5-bis{(4-bromophenyl)amino}cyclohexa-1,4-diene-1,4-dicarboxylate Dimethyl 1,4-cyclohexanedione-2,5-dicarboxylate (4.56 gm; 20 mmol) and methanol (100 ml) were heated to boiling, then 4-bromoaniline (6.88 gm; 40 mmol) was added followed by conc. hydrochloric acid (200 µl). The mixture was refluxed for 5 hours under a nitrogen atmosphere. On cooling a cream solid precipitated out which was collected by filtration, washed with methanol and dried under vacuum to give 10.18 gm (95%) of dimethyl 2,5-bis{(4-bromophenyl)amino}cyclohexa-1,4-diene-1,4-dicaboxylate.

6.2 2,5-Bis{(4-bromophenyl)amino}terephthalic acid

Dimethyl 2,5-bis{(4-bromophenyl)amino]cyclohexa-1,4-diene-1,4-dicarboxylate (5.36 gm; 10 mmol) the sodium salt of 3-nitrobenzenesulphonic acid (2.3 gm; 10 mmol), ethanol (50 ml) and 1.0M sodium hydroxide (30 ml) were heated to reflux for 7 hours under a nitrogen atmosphere. The bright yellow solution was allowed to cool and water (120 ml) was added. The mixture was acidified with conc. hydrochloric acid when a magenta solid precipitated out. This material was filtered off, washed with water and dried under vacuum over phosphorous pentoxide to give 4.84 gm (96%) of 2,5-bis{(4-bromophenyl)amino}terephthalic acid.

6.3 2,9-Dibromoquinacridone 2,5-Bis{(4-bromophenyl)amino}terephthalic acid (4.0 gm; 7.9 mmol) and polyphosphoric acid (34 gm) were heated at 150° C. for 4 hours under a nitrogen atmosphere. The mixture was allowed to cool and then poured into iced water (100 ml) when a magenta solid was formed. The solid was filtered off, washed with water, then methanol and dried under vacuum over phosphorous pentoxide to give 3.68 gm (99%) 2,9-dibromoquinacridone.

6.4 6-{2,9-dibromo-12-(5-carboxypentyl)-7,14-dioxo-7,14-dihydro-12H-quino[2,3-b]acridin-5-yl}hexanoic acid, diethyl ester 2,9-Dibromoquinacridone (2.35 gm; 5.0 mmol) was suspended in anhydrous dimethylformamide (15 ml) under a nitrogen atmosphere. Sodium hydride (60% suspension in oil; 480 mg; 12 mmol) was added and the mixture stirred until effervescence stopped. Anhydrous dimethyl sulphoxide (25 ml) was added. The reaction was heated to 70° C. for 2 hour. Ethyl 6-bromohexanoate (2.67 ml; 15 mmol) was added to the dark green solution and the mixture stirred overnight at 50° C. The dark blue solution was allowed to cool, then the mixture was poured into water (200 ml) and acidified with conc. hydrochloric acid. The solid was filtered off, washed with water and air dried. This was purified by flash chromatography (silica. 5-20% ethyl acetateldichloromethane) to give 1.74 gm (46%) of 6-{2,9-dibromo-12-(5-carboxypentyl)-7,14-dioxo-7,14-dihydro-12H-quino[2,3-b]acridin-5-yl}hexanoic acid, diethyl ester.

$\delta_H$ (200 MHz, CDCl$_3$) 1.25(6H, t), 1.80(12H, m), 2.39 (4H, t), 4.15(4H, dd), 4.39(4H, t), 7.24(2H, d), 7.70(2H, dd), 8.42(4H, s). $\lambda_{max}$(ab) 493 nm, 527 nm $\lambda_{max}$(em) 560 nm, 600 nm. (Dichloromethane).

6.5 6-{2,9-dibromo-12-(5-carboxypentyl)-7,14-dioxo-7,14-dihydro-12H-quino[2,3-b]acridin-5-yl}hexanoic acid 6-{2,9-Dibromo-12-(5-carboxypentyl)-7,14-dioxo-7,14-dihydro-12H-quino[2,3-b]acridin-5-yl}hexanoic acid, diethyl ester (1.0 gm) was dissolved in glacial acetic acid (20 ml) to give a deep magenta solution. 1.0M hydrochloric acid (10 ml) was added and the mixture heated to reflux for 5 hours. The reaction was allowed to cool, the red precipitate filtered off, washed with acetic acid and then diethyl ether and dried under vacuum over phosphorous pentoxide to give 0.86 gm (93%) of 6-{2,9-dibromo-12-(5-carboxypentyl)-7,14-dioxo-7,14-dihydro-12H-quino[2,3-b]acridin-5-yl}hexanoic acid.

Mass spectrum: (ES+) (M+H) 753, 755, 757. $\lambda_{max}$(ab) 499 nm, 533 nm. $\lambda_{max}$(em) 552 nm, 595 nm. (methanol)

7. 6-{2,9-Dichloro-12-(5-carboxypentyl)-7,14-dioxo-7,14-dihydro-12H-quino[2,3-b]acridin-5-yl}hexanoic acid, diethyl ester

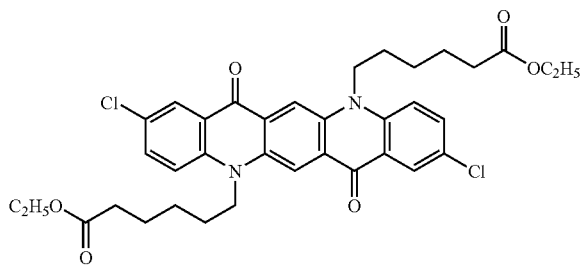

7.1 Dimethyl 2,5-bis{(4-chlorophenyl)amino}cyclohexa-1,4-diene-1,4-dicarboxylate Dimethyl 1,4-cyclohexanedione-2,5-dicarboxylate (4.5 6 gm; 20 mmol) and methanol (100 ml) were heated to boiling; then 4-chloroaniline (5.36 gm; 42 mmol) was added followed by conc. hydrochloric acid (200 µl). The mixture was refluxed for 5 hours under a nitrogen atmosphere. On cooling, a cream solid precipitated out which was collected by filtration, washed with methanol and dried under vacuum to give 8.62 gm (96%) of dimethyl 2,5-bis{(4-chlorophenyl)amino}cyclohexa-1,4-diene-1,4-dicarboxylate.

7.2 2,5-Bis{(4-chlorophenyl)amino}terephthalic acid

Dimethyl 2,5-bis{(4-chlorophenyl)amino}cyclohexa-1,4-diene-1,4-dicarboxylate (4.47 gm, 10 mmol), the sodium salt of 3-nitrobenzenesulphonic acid (2.3 gm; 10 mmol), ethanol (70 ml) and 1.0M sodium hydroxide (40 ml) were heated to reflux overnight under a nitrogen atmosphere. The bright yellow solution was allowed to cool and water (120 ml) was added. The mixture was acidified with conc. hydrochloric acid when a red solid precipitated out. This material was filtered off, washed with water and dried under vacuum over phosphorous pentoxide to give 4.0 gm (96%) of 2,5-bis{(4-chlorophenyl)amino}terephthalic acid.

$\lambda_{max}$(ab) 308 nm, 379 nm. (0.1M sodium hydroxide)
Mass spectrum (ES+) (M+H) 417.

7.3 2,9-Dichloroquinacridone 2,5-Bis{(4-chlorophenyl)amino}terephthalic acid (3.35 gm; 8 mmol) and polyphosphoric acid (30 gm) were heated at 150° C. for 3 hours under a nitrogen atmosphere. The mixture was allowed to cool and then poured into iced water (200 ml) when a magenta solid precipitated out. This was filtered off, washed with water and methanol, then dried under vacuum over phosphorous pentoxide to give 3.1 gm (100%) of 2,9-dichloroquinacridone.

Mass spectrum (ES+) (M+H) 381

7.4 6-{2,9-Dichloro-12-(5-carboxypentyl)-7,14-dioxo-7,14-dihydro-12H-quino[2,3-b]acridin-5-yl}hexanoic acid, diethyl ester 2,9-Dichloroquinacridone (381 mg; 1.0 mmol) was suspended in anhydrous dimethylformamide (4 ml) under a nitrogen atmosphere. Sodium hydride (60% suspension in oil; 100 mg; 2.40 mmol) was added and the mixture stirred until effervescence stopped. Anhydrous dimethyl sulphoxide (7 ml) was added. The reaction was heated to 70° C. for 1 hour. Ethyl 6-bromohexanoate (535 µl; 3.0 mmol) was added to the dark green solution and the mixture stirred overnight at 70° C. The dark orange-red solution was allowed to cool, then the mixture was poured into water (150 ml) and 1.0M hydrochloric acid (10 ml). The solid was filtered off, washed with water and air dried. This was purified by flash chromatography (silica. 20% ethyl acetate/dichloromethane) to give a red oil which crystallised on triturating with diethyl ether to give 205 mg (31%) of 6-{2,9-dichloro-12-(5-carboxy-pentyl)-7,14-dioxo-7,14-dihydro-12H-quino[2,3-b]acridin-5-yl}hexanoic acid, diethyl ester.

Mass spectrum (ES+) (M+H) 665 $\delta_H$ (200 MHz, CDCl$_3$) 1.27(6H, t), 1.80(12H, m), 2.39(4H, t), 4.15(4H, dd), 4.46(4H, t), 7.40(2H, d). 7.64(2H, dd), 8.40(2H, d), 8.6(2H, s) $\lambda_{max}$(ab) 464 nm, 493 nm, 528 nm. $\lambda_{max}$(em) 560 nm, 600 nm. (Dichloromethane).

8. 6-{2,9-Difluoro-12-(5-carboxypentyl)-7,14-dioxo-7,14-dihydro-12H-quino[2,3-b]acridin-5-yl}hexanoic acid, diethyl ester

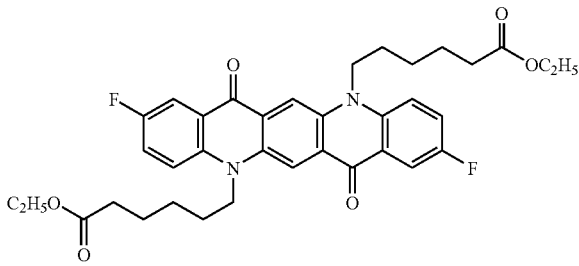

8.1 Dimethyl 2,5-bis{(4-fluorophenyl)amino}cyclohexa-1,4-diene-1,4-dicarboxylate Dimethyl 1,4-cyclohexanedione-2,5-dicarboxylate (9.12 gm; 40 mmol) and methanol (200 ml) were heated to boiling, then 4-fluoroaniline (8.35 ml (9.78 gm); 42 mmol) was added followed by conc. hydrochloric acid (400 µl). The mixture was refluxed for 3 hours under a nitrogen atmosphere. On cooling a yellow solid precipitated out which was collected by filtration, washed with methanol and dried under vacuum to give 15.8 gm (96%) of dimethyl 2,5-bis{(4-fluorophenyl)amino}cyclohexa-1,4-diene-1,4-dicarboxylate.

8.2 2,5-Bis{(4-fluorophenyl)amino}terephthalic acid

Dimethyl 2,5-bis{(4-fluorophenyl)amino}cyclohexa-1,4-diene-1,4-dicarboxylate (6.21 gm, 15 mmol), the sodium salt of 3-nitrobenzenesulphonic acid (3.6 gm; 16 mmol), ethanol (90 ml) and 1.0M sodium hydroxide (50 µl) were heated to reflux overnight under a nitrogen atmosphere. The bright yellow solution was allowed to cool and water (120 ml) was added. The mixture was acidified with conc. hydrochloric acid when a red solid precipitated out. This material was filtered off, washed with water and dried under vacuum over phosphorous pentoxide to give 5.6 gm (97%) of 2,5-bis{(4-fluorophenyl)amino}terephthalic acid $\lambda_{max}$(ab) 295 nm, 380 nm. (0.1M sodium hydroxide)

8.3 2,9-Difluoroquinacridone 2,5-Bis{(4-fluorophenyl)amino}terephthalic acid (5.0 gm; 13 mmol) and polyphosphoric acid (~50 gm) were heated at 150° C. for 3 hours under a nitrogen atmosphere. The mixture was allowed to cool and then poured into iced water (200 ml) when a magenta solid precipitated out. This was filtered off, washed with water and then methanol, then dried under vacuum over phosphorous pentoxide to give 4.5 gm (99%) of 2,9-difluoroquinacridone.
Mass spectrum (ES+) (M+H) 349

8.4 6-{2,9-Difluoro-12-(5-carboxypentyl)-7,14-dioxo-7,14-dihydro-12H-quino[2,3-b]acridin-5-yl}hexanoic acid, diethyl ester 2,9-Difluoroquinacridone (350 mg; 1.0 mmol) was suspended in anhydrous dimethylformamide,(4 ml) under a nitrogen atmosphere. Sodium hydride (60% suspension in oil; 100 mg; 2.40 mmol) was added and the mixture stirred until effervescence stopped. The reaction was heated to 70° C. for 1 hour. Ethyl 6-bromohexanoate (535 µl; 3.0 mmol) was added to the dark green solution and the mixture stirred overnight at 70° C. The dark orange-red solution was allowed to cool; then the mixture was poured into water (150 ml) and 1.0M hydrochloric acid. The solid was filtered off, washed with water and air dried. This was purified by flash chromatography (silica. 20% ethyl acetate/dichloromethane) to give a red oil which crystallised on triturating with diethyl ether to give 171 mg (27%) of 6-{2,9-difluoro-12-(5-carboxypentyl)-7,14-dioxo-7,14-dihydro-12H-quino[2,3-b]acridin-5-yl}hexanoic acid, diethyl ester.

$\delta_H$ (200 MHz, CDCl$_3$) 1.27(6H, t), 1.80(12H, m), 2.39 (4H, t), 4.15(4H, dd), 4.48(4H, t), 7.46(4H, dd), 8.12(2H, d), 8.61(2H, s). $\lambda_{max}$(ab) 495 nm, 533 nm. $\lambda_{max}$(em) 570 nm, 605 nm. (Dichloromethane) Mass spectrum (ES+) (M+H) 633.

9. 6-{2,9-dimethyl-12-(5-carboxypentyl)-7,14-dioxo-7,14-dihydro-12H-quino[2,3-b]acridin-5-yl}hexanoic acid, diethyl ester

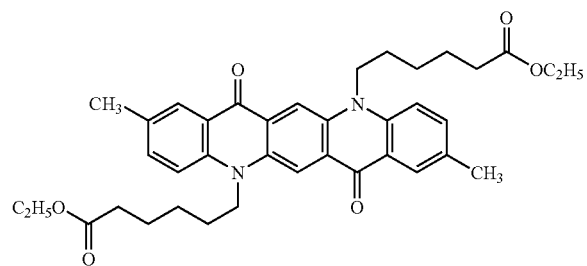

9.1 Dimethyl 2,5-bis{(4-methylphenyl)amino}cyclohexa-1,4-diene-1,4-dicarboxylate Dimethyl 1,4-cyclohexanedione-2,5-dicarboxylate (4.56 gm; 20 mmol) and methanol (100 ml) were heated to boiling; then 4-methylaniline (4.5 gm; 42 mmol) was added followed by conc. hydrochloric acid (200 µl). The mixture was refluxed for 5 hours under a nitrogen atmosphere. On cooling a cream solid precipitated out which was collected by filtration, washed with methanol and dried under vacuum to give 7.92 gm (97%) of dimethyl 2,5-bis{(4-methylphenyl)amino}cyclohexa-1,4-diene-1,4-dicarboxylate.

9.2 2,5-Bis{(4-methylphenyl)amino}terephthalic acid

Dimethyl 2,5-bis{(4-methylphenyl)amino}cyclohexa-1,4-diene-1,4-dicarboxylate (5.1 gm, 12.5 mmol), sodium salt of 3-nitrobenzenesulphonic acid (2.93 gm; 13 mmol), ethanol (75 ml) and 1.0M sodium hydroxide (40 ml) were heated to reflux overnight under a nitrogen atmosphere. The bright yellow solution was allowed to cool and water (120 ml) was added. The mixture was acidified with conc. hydrochloric acid when a purple solid precipitated out. This material was filtered off, washed with water and dried under vacuum over phosphorous pentoxide to give 4.53 gm is (96%) of 2,5-bis{(4-chlorophenyl)amino}terephthalic acid.

$\lambda_{max}$(ab) 299 nm, 386 nm. (0.1M sodium hydroxide).

9.3 2,9-Dimethylquinacridone 2,5-Bis{(4-methylphenyl)amino}terephthalic acid (3.76 gm; 10 mmol) and polyphosphoric acid (40 gm) were heated at 150° C. for 2.5 hours under a nitrogen atmosphere. The mixture was allowed to cool and then poured into iced water (100 ml) when a magenta solid precipitated out. This was filtered off, washed with water and then methanol, then dried under vacuum over phosphorous pentoxide to give 3.12 gm (92%) of 2,9-dimethylquinacridone.

9.4 6-{2,9-Dimethyl-12-(5-carboxypentyl)-7,14-dioxo-7,14-dihydro-12H-quino[2,3-b]acridin-5-yl}hexanoic acid, diethyl ester 2,9-Dimethylquinacridone (680 mg; 2.0 mmol) was suspended in a mixture of anhydrous dimethylformamide (10 ml) and anhydrous dimethyl sulphoxide (10 ml) under a nitrogen atmosphere. Sodium hydride (60% suspension in oil; 200 mg; 5.0 mmol) was added and the mixture stirred until effervescence stopped. The reaction was heated to 70° C. for 1 hour. Ethyl 6-bromohexanoate (1.07 ml (1.34 gm); 6.0 mmol) was added to the dark blue-green solution and the mixture stirred overnight at 60° C. The dark orange-red solution was allowed to cool, then the mixture was poured into water (150 ml) and 1.0M hydrochloric acid (30 ml). The solid was filtered off, washed with water and air dried. This was purified by flash chromatography (silica, 5-25% ethyl acetate/dichloromethane) to give a red oil which crystallised on triturating with diethyl ether to give 780 mg (62%) of 6-{2,9-dimethyl-12-(5-carboxypentyl)-7,14-dioxo-7,14-dihydro-12H-quino[2,3-b]acridin-5-yl}hexanoic acid, diethyl ester.

$\delta_H$ (200 MHz, CDCl$_3$) 1.24 (6H, t), 1.80(12H, m), 2.38 (10H, m), 4.15(4H, dd), 4.45(4H, t), 7.30(2H dd), 7.47(2H, dd), 8.21(2H, d), 8.57(2H, s). $\lambda_{max}$(ab) 495 nm, 530 nm $\lambda_{max}$(em) 545 nm. (Dichloromethane).

10. 6-{2,9-Dimethoxy-12-(5-carboxypentyl)-7,14-dioxo-7,14-dihydro-12H-quino[2,3-b]acridin-5-yl}hexanoic acid, diethyl ester

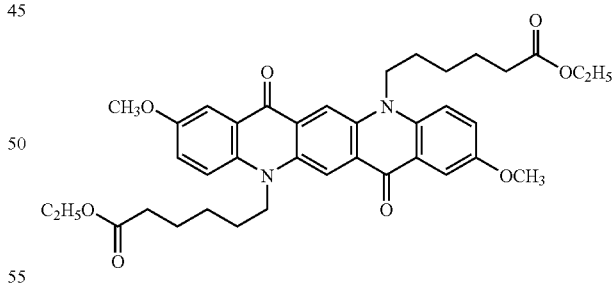

10.1 Dimethyl 2,5-bis{(4-methoxyphenyl)amino}cyclohexa-1,4-diene-1,4-dicarboxylate Dimethyl 1,4-cyclohexanedione-2,5-dicarboxylate (9.12 gm; 40 mmol) and methanol (200 ml) were heated to boiling, then 4-methoxyaniline (10.84 gm; 88 mmol) was added followed by conc. hydrochloric acid (400 µl). The mixture was refluxed for 2.5 hours under a nitrogen atmosphere. On cooling, an orange solid precipitated out which was collected by filtration, washed with methanol and dried under vacuum to give 17.0 gm (97%) of dimethyl 2,5-bis{(4-methoxyphenyl)amino}cyclohexa-1,4-diene-1,4-dicarboxylate.

10.2 2,5-Bis{(4-methoxyphenyl)amino}terephthalic acid

Dimethyl 2,5-bis{(4-methoxyphenyl)amino}cyclohexa-1,4-diene-1,4-dicarboxylate (6.58 gm, 15 mmol), the sodium salt of 3-nitrobenzenesulphonic acid (3.6 gm; 16 mmol), ethanol (90 ml) and 1.0M sodium hydroxide (50 ml) were heated to reflux overnight under a nitrogen atmosphere. The orange solution was allowed to cool and water (120 ml) was added. The mixture was acidified with conc. hydrochloric acid when a purple solid precipitated out. This material was filtered off, washed with water, then 25% ethanol/water and dried under vacuum over phosphorous pentoxide to give 6.0 gm (98%) of 2,5-bis{(4-methoxyphenyl)amino}terephthalic acid.

$\lambda_{max}$(ab) 299 nm, 392 nm. (0.1M sodium hydroxide).

10.3 2,9-Dimethoxyquinacridone 2,5-Bis{(4-methoxyphenyl)amino}terephthalic acid (1.02 gm; 2.5 mmol) and polyphosphoric acid (10 gm) were heated at 160° C. for 15 minutes under a nitrogen atmosphere. The mixture was allowed to cool and then poured into iced water (200 ml) when a purple solid precipitated out. This was filtered off, washed with water and methanol, then dried under vacuum over phosphorous pentoxide to give 948 mg (100%) of 2,9-dimethoxyquinacridone.

Mass spectrum (ES+) (M+H) 373.

10.4 Diethyl ester of 6-{2,9-dimethoxy-12-(5-carboxypentyl)-7,14-dioxo-7,14-dihydro-12H-quino[2,3-b]acridin-5-yl}hexanoic acid.

2,9-Dimethoxyquinacridone (375 mg; 1.0 mmol) was suspended in a mixture of anhydrous dimethylformamide (5 ml) and anhydrous dimethyl sulphoxide (5 ml) under a nitrogen atmosphere. Sodium hydride (60% suspension in oil; 100 mg; 2.40 mmol) was added and the mixture stirred until effervescence stopped. The reaction was heated to 70° C. for 1 hour. Ethyl 6-bromohexanoate (535 µl; 3.0 mmol) was added to the dark green solution and the mixture stirred overnight at 70° C. The dark purple-red solution was allowed to cool, then the mixture was poured into water (150 ml) and 1.0M hydrochloric acid (20 ml). The solid was filtered off, washed with water and air dried. This was purified by flash chromatography (silica. 5-30% ethyl acetate/dichloromethane) to give 230 mg (35%) of 6-{2,9-dimethoxy-12-(5-carboxypentyl)-7,14-dioxo-7,14-dihydro-12H-quino[2,3-b]acridin-5-yl}hexanoic acid, diethyl ester as a red solid. $\delta_H$ (200 MHz, CDCl$_3$) 1.25(6H, t), 1.80(12H, m), 2.40(4H, t), 4.00(6H, s), 4.15(4H, m), 4.50(4H, t ), 7.42(4H, m), 7.91(2H, d), 8.70(2H, s). $\lambda_{max}$(ab) 510 nm, 547 nm. $\lambda_{max}$(em) 592 nm. (methanol).

Mass spectrum (ES+) (M+H) 656 (M+Na) 679.

11. 6-{2,9-Dinitro-12-(5-carboxypentyl)-7,14-dioxo-7,14-dihydro-12H-quino[2,3-b]acridin-5-yl}hexanoic acid, diethyl ester

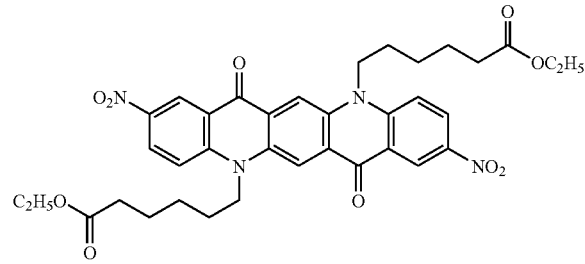

5,12-Bis(O-ethyl-6-hexanoyl)-5,12-dihydroquino[2,3-b]acridin-7,14-dione (300 mg; 0.5 mmol) was cooled in an ice bath and then dissolved in conc. sulphuric acid (3 ml) under a nitrogen atmosphere to give a purple solution. Conc. nitric acid (70 µl; 1.08 mmol) was added and the reaction mix removed from the ice bath. After one hour, the reaction mix was added to ice when an orange precipitate formed. The mixture was extracted with dichloromethane. The organic phase was washed with dilute sodium bicarbonate solution, then dried with anhydrous magnesium sulphate. After filtration, the solvent was removed by rotary evaporation to give an orange solid. This was purified by flash chromatography (silica. 2-3% methanol/dichloromethane). After removal of solvent, the residue was triturated with diethyl ether to give 240 mg (70%) of 6-{2,9-dinitro-12-(5-carboxypentyl)-7,14-dioxo-7,14-dihydro-12H-quino[2,3-b]acridin-5-yl}hexanoic acid, diethyl ester as an orange solid.

$\delta_H$ (200 MHz, CD$_3$OD) 1.28(6H, t), 1.80(12H, m), 2.43(4H, t), 4.17(4H, dd), 4.56(4H, t), 7.56(2H, d), 8.48(2H, dd), 8.66(2H, s), 9.30(2H, d). $\lambda_{max}$(ab) 408 nm, 474 nm, 506 nm. $\lambda_{max}$(em) 518 nm, 556 nm. (Dichloromethane).

N.B. This material has very weak or is non-fluorescent in DMF, DMSO and methanol.

12. Fluorescence Lifetime Studies

Figure 2:
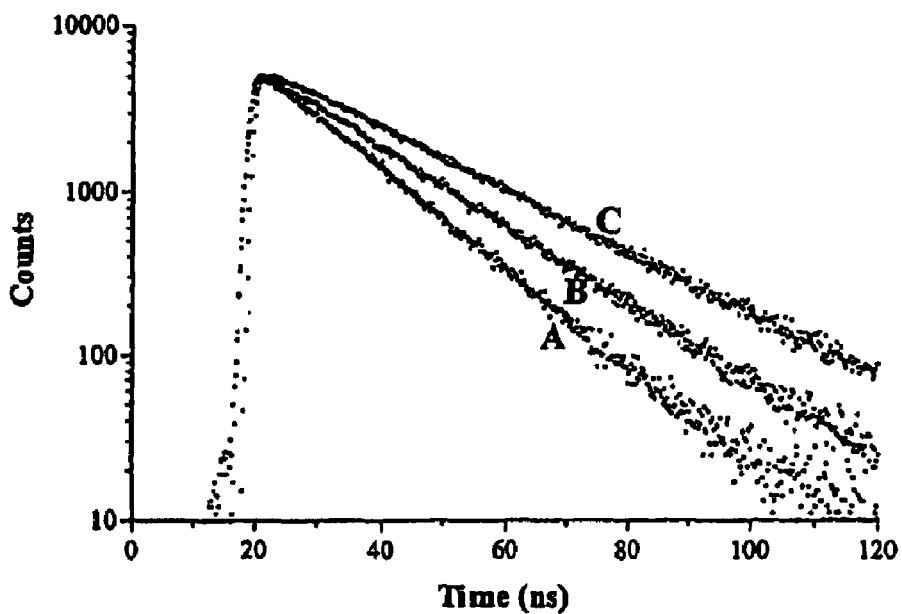
FIG. 2 shows the fluorescence lifetime decay plots of three dyes according to the present invention.

FIG. 2 is a plot showing the fluorescence lifetimes of certain dyes according to the invention. Fluorescence lifetimes of a range of dyes were determined by a time-correlated single photon counting technique using an Edinburgh Instruments FL900 CDT Time-Resolved Fluorometer. Samples were excited at 500 nm using a hydrogen-filled flashlamp. Detection was at 550 nm. Deconvolution using a non-linear least-squares algorithm gave the results shown in Table 2.

TABLE 2

| Fluorescence Lifetimes | | |
| --- | --- | --- |
| Compound | Solvent | Lifetime |
| 5,12-Di-n-hexylquinacridone | CH$_2$Cl$_2$/MeOH | 26.5 nsec |
| 2,4,9,11-Quinacridone tetrasulphonic acid | water | 22.1 nsec |
| 2,9-Quinacridone disulphonic acid | water | 20.6 nsec |
| 6-(7,14-Dioxo-2,9-disulpho-7,14-dihydro-12H-quino[2,3-b]acridin-5-yl)hexanoic acid | water | 20.1 nsec |
| Quinacridone | DMSO | 22 nsec |
| 2-Bromo-5,12-di-n-hexylquinacridone | CH$_2$Cl$_2$/MeOH | 20.4 nsec |
| 2,9-Dibromo-5,12-di-n-hexylquinacridone | CH$_2$Cl$_2$/MeOH | 16.9 nsec |
| 6-(12-Ethyl-7,14-dioxo-2,9-disulpho-7,14- | water | 22.7 nsec |

TABLE 2-continued

Fluorescence Lifetimes

| Compound | Solvent | Lifetime |
|---|---|---|
| dihydro-12H-quino[2,3-b]acridin-5-yl) hexanoic acid | | |
| 6-{2,9-Dibromo-12-(5-carboxypentyl)-7,14-dioxo-7,14-dihydro-12H-quino[2,3-b]acridin-5-yl}hexanoic acid, diethyl ester. | water | 18.0 nsec |
| 6-{2,9-Dibromo-12-(5-carboxypentyl)-7,14-dioxo-7,14-dihydro-12H-quino[2,3-b]acridin-5-yl}hexanoic acid. | MeOH/water | 20.7 nsec 17.7 nsec |
| 6-{2,9-Dichloro-12-(5-carboxypentyl)-7,14-dioxo-7,14-dihydro-12H-quino[2,3-b]acridin-5-yl}hexanoic acid, diethyl ester. | MeOH | 22.3 nsec |
| 6-{2,9-Difluoro-12-(5-carboxypentyl)-7,14-dioxo-7,14-dihydro-12H-quino[2,3-b]acridin-5-yl}hexanoic acid, diethyl ester. | MeOH | 21.4 nsec |
| 6-{2,9-Dimethyl-12-(5-carboxypentyl)-7,14-dioxo-7,14-dihydro-12H-quino[2,3-b]acridin-5-yl}hexanoic acid, diethyl ester | MeOH | 21.9 nsec |
| 6-{2,9-Dimethoxy-12-(5-carboxypentyl)-7,14-dioxo-7,14-dihydro-12H-quino[2,3-b]-acridin-5-yl}hexanoic acid, diethyl ester. | EtOH | 14.0 nsec |
| 6-{2,9-Dinitro-12-(5-carboxypentyl)-7,14-dioxo-7,14-dihydro-12H-quino[2,3-b]acridin-5-yl}hexanoic acid, diethyl ester. | $CH_2Cl_2$ | 17.0 nsec |

13. Protein Labelling

13.1 Preparation of a conjugate of 6-{7,14-dioxo-2,9-disulpho-7,14-dihydro-12H-quino[2,3-b]acridin-5-yl}hexanoic acid with ovalbumin To 10 ml of ovalbumin (1 mg/ml in 0.1M carbonate buffer, pH 9.3) was added 100 μl of O—(N-succinimidyl)-6-{7,14-dioxo-2,9-disulpho-7,14-dihydro-12H-quino[2,3-b]acridin-5-yl}hexanoic acid (1 mg/100 μl in DMSO) dropwise whilst stirring. Gentle stirring continued for 1 hr at ambient temperature in a foil wrapped vial. Unconjugated dye was removed by overnight dialysis (12-14K MWCO) at +4° C. with at least 2 changes of PBS. The dye-conjugate (Conjugate A) was recovered and stored at +4° C.

13.2 Determination of the Fluorescence Lifetimes of 6-{7,14-dioxo-2,9-disulpho-7,14-dihydro-12H-quino[2,3-b]acridin-5-yl}hexanoic acid and its conjugate with ovalbumin (Conjugate A)

Figure 3:
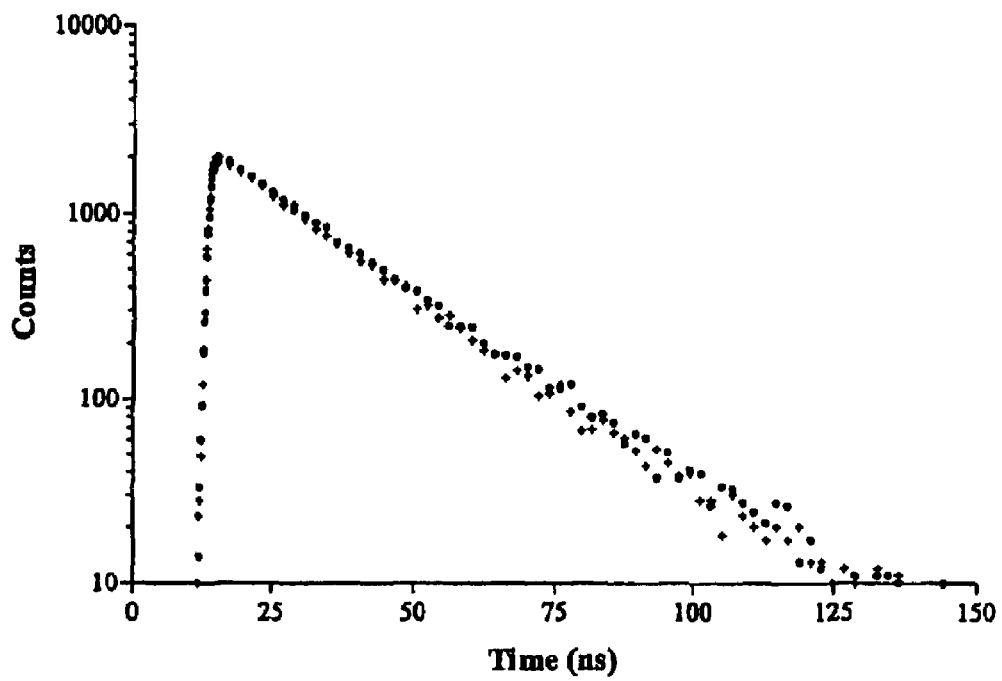
FIG. 3 is a lifetime decay plot of 6-{7,14-dioxo-2,9-disulpho-7,14-dihydro-12H-quino[2,3-b]acridin-5-yl}hexanoic acid and of its conjugate with ovalbumin.

The fluorescence lifetimes of 6-{7,14-dioxo-2,9-disulpho-7,14-dihydro-12H-quino[2,3-b]acridin-5-yl}hexanoic acid and its conjugate with ovalbumin (Conjugate A) was determined in PBS. The results are shown in FIG. 3. Deconvolution and curve fitting using a non-linear least-squares algorithm gave the results shown in Table 3.

TABLE 3

Fluorescence Lifetimes

| Name | Lifetime (nsec) |
|---|---|
| 6-{7,14-Dioxo-2,9-disulpho-7,14-dihydro-12H-quino[2,3-b]acridin-5-yl}hexanoic acid | 20.1 |
| 6-{7,14-Dioxo-2,9-disulpho-7,14-dihydro-12H-quino[2,3-b]acridin-5-yl}hexanoic acid - Ovalbumin conjugate (Conjugate A) | 19.8 |

14. Labelling of MMP3 peptide substrate with O—{N-succinimidyl-6-(12-ethyl-7,14-dioxo-2,9-disulpho-7,14-dihydro-12H-quino[2,3-b]acridin-5-yl}hexanoate The MMP3 peptide substrate ($NH_2$-RPKPVE(Nva)WRK-$NH_2$) was synthesised on a Applied Biosystems model 431A peptide synthesiser using standard Fmoc chemistry and Rink amide resin. At the end of the synthesis the N-terminal Fmoc group was removed. The partially protected peptide was left attached to the solid support, in which form it was reacted with O—{N-succinimidyl-6-(12-ethyl-7,14-dioxo-2,9-disulpho-7,14-dihydro-12H-quino[2,3-b] acridin-5-yl}hexanoate. The labelled peptide was then cleaved from the solid support using standard techniques and then purified by reverse phase HPLC.

50 mg of the resin bound peptide (equivalent to 16 μmoles of peptide) was weighed into a 1.5 ml screw top polypropylene V-vial to which was added 12 mg (16 μmoles) of O-{N-succinimidyl-6-(12-ethyl-7,14-dioxo-2,9-disulpho-7,14-dihydro-12H-quino[2,3-b]acridin-5-yl}hexanoic acid dissolved in 1 ml of anhydrous DMSO followed by 20 μl of diisopropylethylamine. The vial was placed on rollers with light excluded for 20 hrs at ambient temperature (22° C.). The resin was then filtered off using a sintered glass frit, washed with 5 ml dry DMSO, 5 ml methanol and finally 5 ml dichloromethane, then dried in vacuo for 2 hrs.

The resin was placed in a small round bottomed flask to which was added 2 ml of an ice cold solution of trifluoroacetic acid (1.9 ml), water (50 1) and triisopropylsilane (TIS)(50 μl). The mixture was stirred magnetically for 90 minutes and allowed to warm to ambient temperature. The mixture was then filtered through a glass wool plug and allowed to drip into 10 ml of ice cold diethyl ether. The pale yellow precipitate was spun down, the supernatant removed, the precipitate redissolved in 1 ml trifluoroacetic acid and reprecipitated in 10 ml ice cold ether. The precipitate was spun down, washed twice with ether then dried in vacuo.

The crude labelled peptide was dissolved in water, filtered through a 0.45 um Millipore filter and a portion was purified on a 25 cm×1 cm C-18 Phenomenex Jupiter column (code 00G-4055-N0) using a gradient of 0.1% TFA/water to 100% of 0.1% TFA/acetonitrile over 30 minutes and a flow of 4 ml/minute. Detection was at 220 and 500 nm. One major peaks was eluted after 13 minutes. The material was freeze dried to give 11.4 mg (6.0 μm) of a red solid.

Mass spectrum (ES+) (M+H) 1893 (calculated molecular weight of quinacridone labelled peptide=1892).

15. Trypsin Cleavage of a Conjugate of Albumin with 6-{12-Ethyl-7,14-dioxo-2,9-disulpho-7,14-dihydro-12H-quino[2,3-b]acridin-5-yl}hexanoic acid Monitored by Fluorescence Polarisation

15.1 Preparation of Albumin Conjugate

To 10 ml of human serum albumin (2 mg/ml in 0.1M carbonate buffer, pH9.3), was added O—{N-succinimidyl-6-(12-ethyl-7,14-dioxo-2,9-disulpho-7,14-dihydro-12H-quino[2,3-b]acridin-5-yl}hexanoate (110 μl; 2 mg/ml in DMSO) dropwise whilst stirring. Gentle stirring continued for 1 hr at ambient temperature in a foil wrapped vial. A Sephadex G25 column (PD10—Amersham Biosciences) was used to purify the conjugate which was eluted in de-ionised water.

15.2 Trypsin Cleavage of Albumin Conjugate

Figure 4:
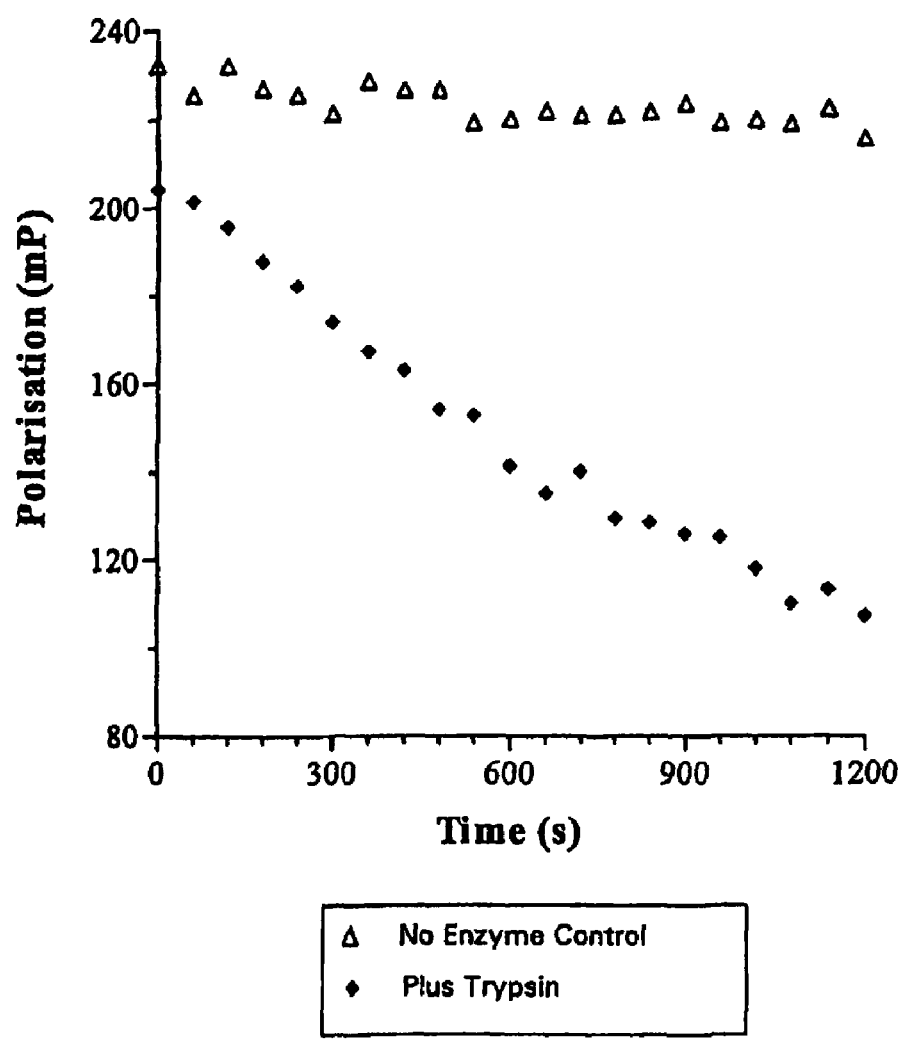
FIG. 4 is a plot showing trypsin cleavage of a conjugate of albumin with 6-{12-ethyl-7,14-dioxo-2,9-disulpho-7,14-dihydro-12H-quino[2,3-b]acridin-5-yl}hexanoic acid monitored by fluorescence polarisation.

To 10 μl of the conjugate (20 μg) in 2 ml of buffer (20 mM Tris pH 7.5; 200 mM NaCl; 6 mM $CaCl_2$) in a cuvette, either 50 μl buffer (as no enzyme control) or 50 μl (500 μg) of trypsin was added. Measurement of the fluorescence polarisation signal was performed using a FluoroMax-3 spectrofluorometer (JYHoriba), with excitation at 485 nm, and detection at 555 nm for 20 minutes at ambient temperature. The results as illustrated in FIG. 4, show that the signal becomes less polarised as the albumin conjugate is cleaved into smaller fragments by trypsin, as expected from polarisation theory.

What is claimed is:

1. A compound having the formula:

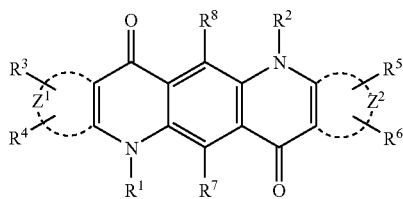

wherein:
groups $R^3$ and $R^4$ are attached to the $Z^1$ ring structure and groups $R^5$ and $R^6$ are attached to the $Z^2$ ring structure;
$Z^1$ and $Z^2$ independently represent the atoms necessary to complete a phenyl ring structure;
at least one of groups $R^1$ and $R^2$ is the group -E-F, wherein E is a spacer group selected from the group consisting of:
$(CHR')_p-$
$-\{(CHR')_q-O-(CHR')_r\}_s-$
$-\{(CHR')_q-NR'-(CHR')_r\}_s-$
$-\{(CHR')_q-(CH=CH)-(CHR')_r\}_s-$
$-\{(CHR')_q-Ar-(CHR')_r\}_s-$
$-\{(CHR')_q-CO-NR'-(CHR')_r\}_s-$ and
$-\{(CHR')_q-CO-Ar-NR'-(CHR')_r\}_s-$
where R' is hydrogen, $C_1-C_4$ alkyl or aryl, which may be optionally substituted with sulphonate, Ar is phenylene, optionally substituted with sulphonate, p is 1-10, q is 0-10, r is 1-10 and s is 1-5;
and F is a reactive group selected from the group consisting of carboxyl, succinimidyl ester, sulpho-succinimidyl ester, isothiocyanate, maleimide, haloacetamide, acid halide, hydrazide, vinylsulphone, dichlorotriazine and phosphoramidite;
groups $R^3$, $R^4$, $R^5$, $R^6$, $R^7$ and $R^8$ are independently selected from hydrogen, halogen, amide, hydroxyl, cyano, nitro, $C_1-C_6$ alkoxy, $C_1-C_{20}$ alkyl, sulphonate, and sulphonic acid;
when any of groups $R^1$ and $R^2$ is not said group -E-F, said remaining group $R^1$ or $R^2$ is selected from hydrogen, mono- or di-nitro-substituted benzyl, $C_1-C_{20}$ alkyl, and the group $-(CH_2-)_n Y$;
Y is selected from sulphonate, sulphate, phosphonate, phosphate, quaternary ammonium and carboxyl; and n is an integer from 1 to 6.

2. The compound of claim 1, wherein said compound is a fluorescent dye and further wherein:
groups $R^3$, $R^4$, $R^5$, $R^6$, $R^7$ and $R^8$ are independently selected from hydrogen, halogen, amide, hydroxyl, cyano, $C_1-C_6$ alkoxy, acrylate, vinyl, styryl, aryl, heteroaryl, $C_1-C_{20}$ alkyl, sulphonate, and sulphonic acid; and
remaining groups $R^1$ and $R^2$ are independently selected from hydrogen, $C_1-C_{20}$ alkyl, and the group $-(CH_2-)_n Y$.

3. The compound of claim 1, wherein said compound is a non-fluorescent or substantially non-fluorescent dye and further wherein at least one of groups $R^1$, $R^2$, $R^3$, $R^4$, $R^5$, $R^6$, $R^7$ and $R^8$ comprises at least one nitro group.

4. The compound of claim 1, wherein group -E-F is selected from:

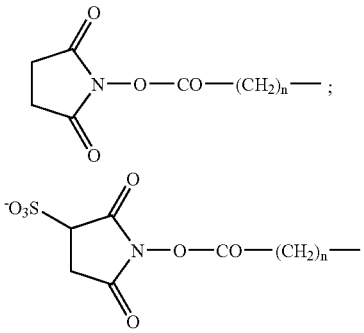

wherein n is an integer from 1-10.

5. The compound of claim 4, wherein n is 5.

6. A compound selected from:
i) O—(N-succinimidyl)-6-(7,14-dioxo-2,9-disulpho-7,14-dihydro-12H-quino[2,3-b]acridin-5-yl)hexanoate; and
ii) O—{N-succinimidyl-6-(12-ethyl-7,14-dioxo-2,9-disulpho-7,14-dihydro-12H-quino[2,3-b]acridin-5-yl)}hexanoate.

* * * * *